United States Patent
Pulé et al.

(10) Patent No.: US 11,879,016 B2
(45) Date of Patent: *Jan. 23, 2024

(54) CHIMERIC ANTIGEN RECEPTOR

(71) Applicant: AUTOLUS LIMITED, London (GB)

(72) Inventors: Martin Pulé, London (GB); John Anderson, London (GB); Simon Thomas, London (GB)

(73) Assignee: AUTOLUS LIMITED, London (GB)

( * ) Notice: Subject to any disclaimer, the term of this patent is extended or adjusted under 35 U.S.C. 154(b) by 264 days.

This patent is subject to a terminal disclaimer.

(21) Appl. No.: 17/196,670

(22) Filed: Mar. 9, 2021

(65) Prior Publication Data

US 2021/0403596 A1 Dec. 30, 2021

Related U.S. Application Data

(63) Continuation of application No. 15/123,331, filed as application No. PCT/GB2015/050649 on Mar. 6, 2015, now Pat. No. 10,975,162.

(30) Foreign Application Priority Data

Mar. 6, 2014 (GB) ..................................... 1403972

(51) Int. Cl.
| | |
|---|---|
| C07K 16/30 | (2006.01) |
| C07K 14/725 | (2006.01) |
| C07K 14/705 | (2006.01) |
| A61K 35/17 | (2015.01) |
| A61K 38/17 | (2006.01) |
| A61K 39/395 | (2006.01) |
| C12N 15/85 | (2006.01) |
| A61K 39/00 | (2006.01) |

(52) U.S. Cl.
CPC .......... *C07K 16/3084* (2013.01); *A61K 35/17* (2013.01); *A61K 38/179* (2013.01); *A61K 38/1774* (2013.01); *A61K 39/39558* (2013.01); *C07K 14/7051* (2013.01); *C07K 14/70517* (2013.01); *C07K 14/70521* (2013.01); *C07K 14/70578* (2013.01); *C12N 15/85* (2013.01); *A61K 2039/505* (2013.01); *C07K 2317/21* (2013.01); *C07K 2317/24* (2013.01); *C07K 2317/52* (2013.01); *C07K 2317/53* (2013.01); *C07K 2317/565* (2013.01); *C07K 2317/622* (2013.01); *C07K 2317/73* (2013.01); *C07K 2319/00* (2013.01); *C07K 2319/03* (2013.01); *C07K 2319/20* (2013.01); *C07K 2319/30* (2013.01); *C12N 2510/00* (2013.01)

(58) Field of Classification Search
None
See application file for complete search history.

(56) References Cited

U.S. PATENT DOCUMENTS

| | | |
|---|---|---|
| 10,925,943 B2 | 2/2021 | Pule et al. |
| 2013/0216528 A1 | 8/2013 | Cheung et al. |
| 2015/0093401 A1 | 4/2015 | Pule et al. |

FOREIGN PATENT DOCUMENTS

| | | |
|---|---|---|
| CL | 201301645 | 6/2013 |
| CL | 201600734 | 3/2016 |
| CL | 201601134 | 5/2016 |
| CL | 201601135 | 5/2016 |
| CL | 201602195 | 9/2016 |
| CL | 201700438 | 2/2017 |
| CL | 201702150 | 8/2017 |
| CL | 201702413 | 9/2017 |
| CN | 103145849 A | 6/2013 |
| RU | 2366664 C2 | 9/2009 |
| RU | 2462476 C2 | 9/2012 |
| WO | WO-01/23573 A1 | 4/2001 |
| WO | WO-2012/033885 A1 | 3/2012 |
| WO | WO-2012/079000 A1 | 6/2012 |
| WO | WO-2013/040371 A2 | 3/2013 |
| WO | WO-2013/040557 A2 | 3/2013 |
| WO | WO-2013/153391 A1 | 10/2013 |
| WO | WO-2015/052538 A1 | 4/2015 |
| WO | WO-2015/075469 A1 | 5/2015 |
| WO | WO-2015/075470 A1 | 5/2015 |
| WO | WO-2015/132598 A1 | 9/2015 |
| WO | WO-2016/030691 A1 | 3/2016 |
| WO | WO-2016/138038 A1 | 9/2016 |
| WO | WO-2016/151315 A1 | 9/2016 |

OTHER PUBLICATIONS

Auten et al., "Effect of scaffold Attachment Region on Transgene Expression in Retrovirus Vector-Transduced Primary T Cells and Macrophages," Human Gene Therapy, 10(8):1389-1399 (1999).

Cooper et al., "Enhanced Transgene Expression in quiescent and Activated Human CD8+ T Cells," Human Gene Therapy, 15:648-658 (2004).

Curran et al., "Chimeric Antigen Receptors for T Cell Immunotherapy: Current Understanding and Future Direction", Journal of Gene Medicine 14(6):405-415 (2012).

(Continued)

*Primary Examiner* — Michael D Burkhart

(74) *Attorney, Agent, or Firm* — MARSHALL, GERSTEIN & BORUN LLP

(57) ABSTRACT

Provision of a chimeric antigen receptor (CAR) comprising a disialoganglioside (GD2)-binding domain which comprises •a) a heavy chain variable region (VH) having complementarity determining regions (CDRs) with the following sequences: •b) a light chain variable region (VL) having CDRs with the following sequences: T cells expressing such a CAR are useful in the treatment of some cancers.

2 Claims, 19 Drawing Sheets

Specification includes a Sequence Listing.

(56) References Cited

OTHER PUBLICATIONS

Esser et al., NK cells engineered to express a GD2-specific antigen receptor display built in ADCC-like activity against tumour cells of neuroectodermal origin. *J. Cell. Mol. Med.* 16: 569-81 (2012).

Grada et al., "Targeting Lung Cancer using GD2-specific T cells", Abstract No. 833 (p. 43), ASGCT Final Program Addendum, American Society of Gene & Cell Therapy, 15th Annual Meeting, May 16-19 (2012).

International Search Report and Written Opinion from International Application No. PCT/GB2015/050649 dated Jun. 2, 2015.

Kim, "Improved Expression Vector Activity Using Insulators and Scaffold/Matrix-Attachment Regions for Enhancing Recombinant Protein Production," Bioprocess International, Suppl. pp. 24-31 (2006).

Nakamura et al., Construction of humanized anti-ganglioside monoclonal antibodies with potent immune effector functions. Cancer Immunol. Immunother. 50(5): 275-84 (2001).

Rudikoff et al., "Single Amino Acid Substitution Altering Antigen-binding Specificity," PNAS 79:1979-1983 (1982).

Schmid et al., J. Immunol. 184:4936-4946 (2010).

Shirasu et al., "Funtional Design of Chimeric T-Cell Antigen Receptors for Adoptive Ummunotherapy of Cancer: Architecture and Outcomes," Anticancer Research 32:2377-2384 (2012).

Straathof et al., "Optimized Anti-GD2/Suicide Gene Cassette and Scale-Up for a Next Generation GD2 Chimeric Antigen Receptor Study for Neuroblastoma," Molecular Therapy, 22(1):S284, Abstract 734 (2014).

Thomas et al., "An Optimized GD2-Targeting Retroviral Cassette for More Potent and Safer Cellular Therapy of Neuroblastoma and Other Cancers", PLOS ONE, 11(3)E0152196, 19 pages (2016).

Tur et al., "An Anti-GD2 Single Chain Fv Selected by Phage Display and Fused to Pseudomonas Exotoxin A Develops Specific Cytotoxic Activity Against Neuroblastoma Derived Cells Lines," International Journal of Molecular Medicine 8:579-584 (2001).

Yvon et al., Immunotherapy of metastatic melanoma using genetically engineered GD2-specific T cells. *Clin. Cancer Res.* 15: 5852-60 (2009).

Zhong et al., PNAS 110:6973-6978 (2013).

FIGURE 4
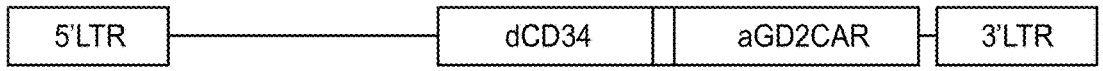
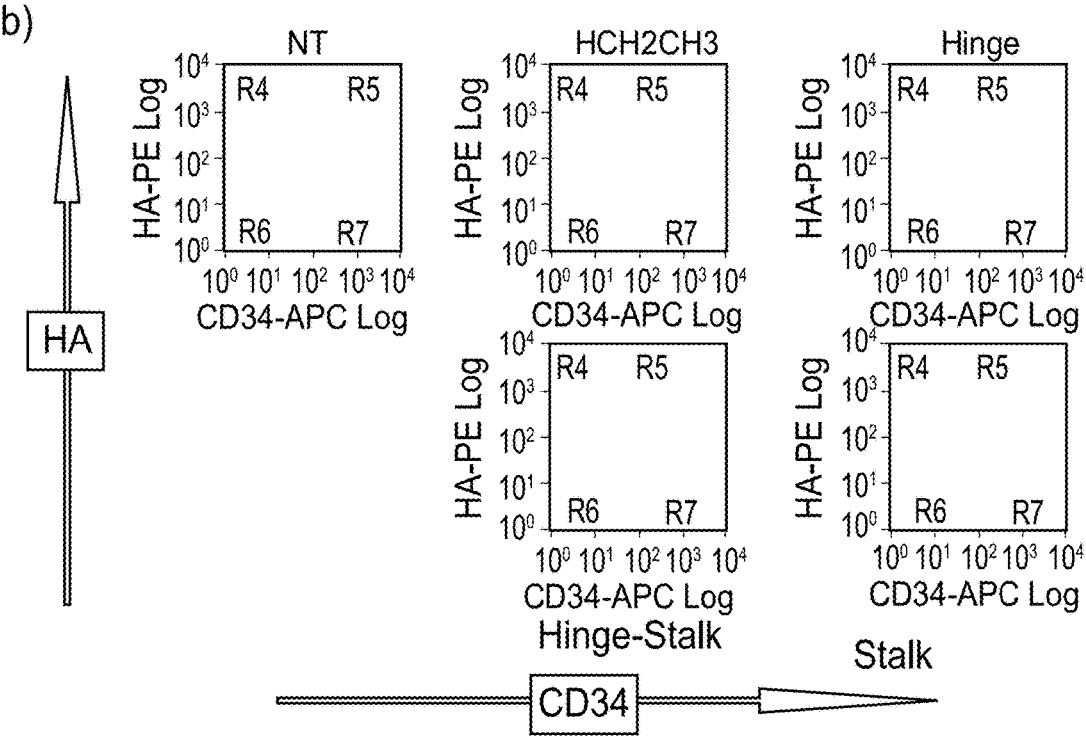
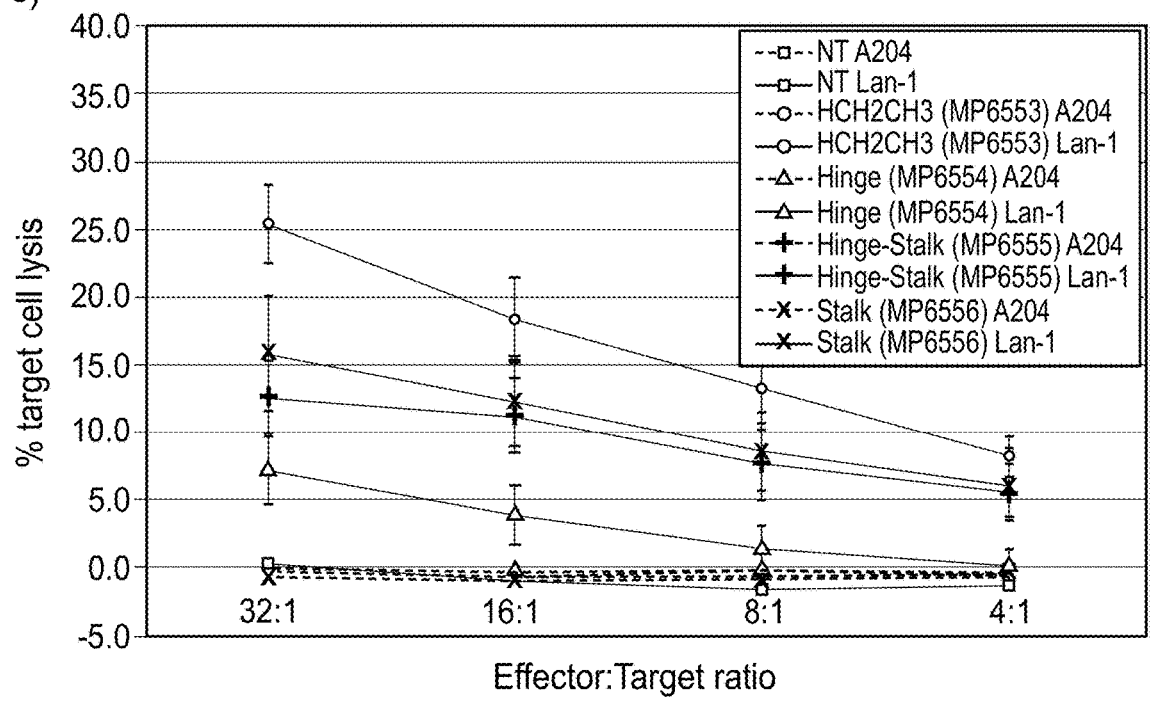

FIGURE 4
d)
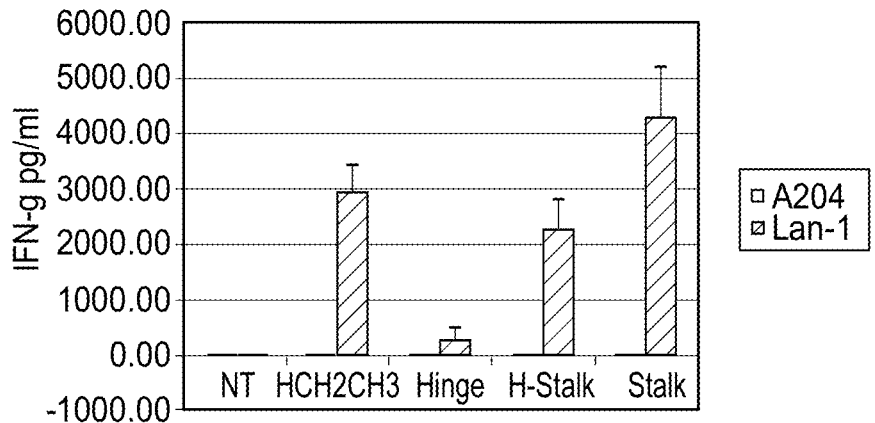
e)
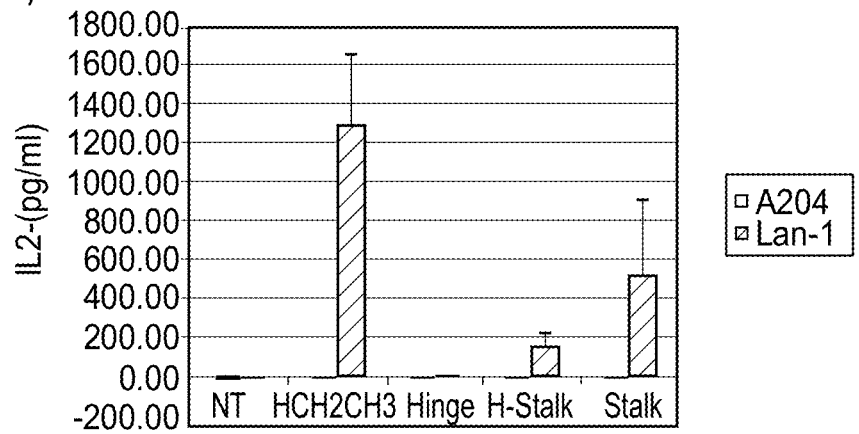
f)
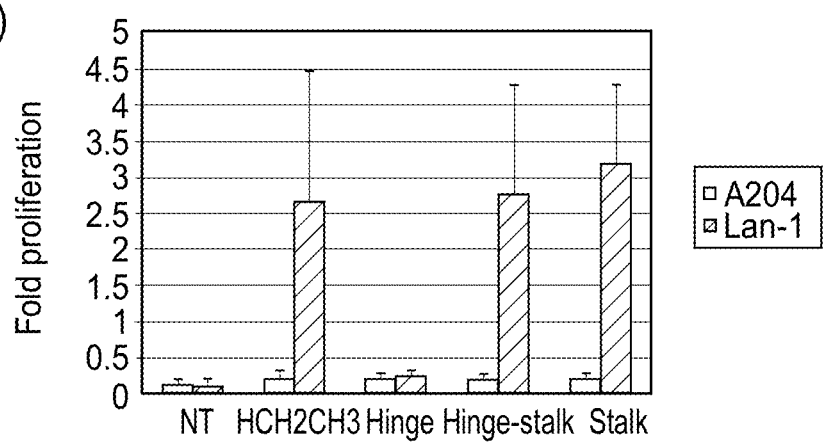

FIGURE 6
a)
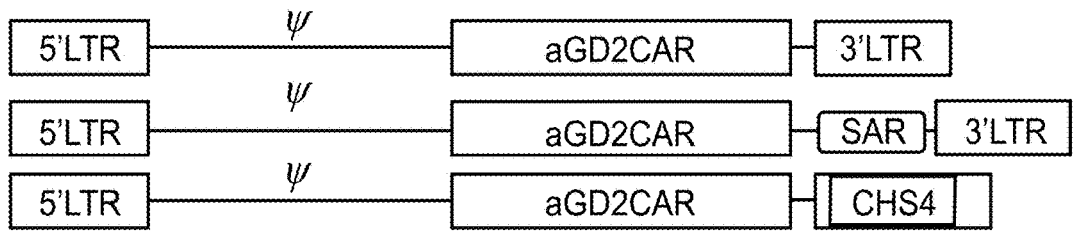
b)
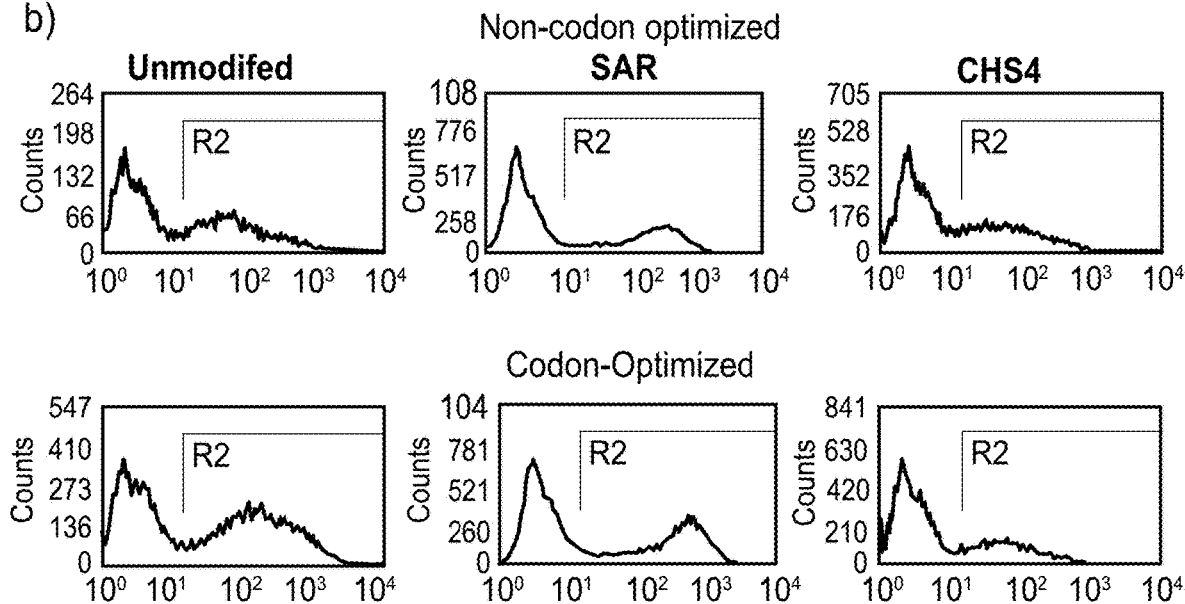
c)
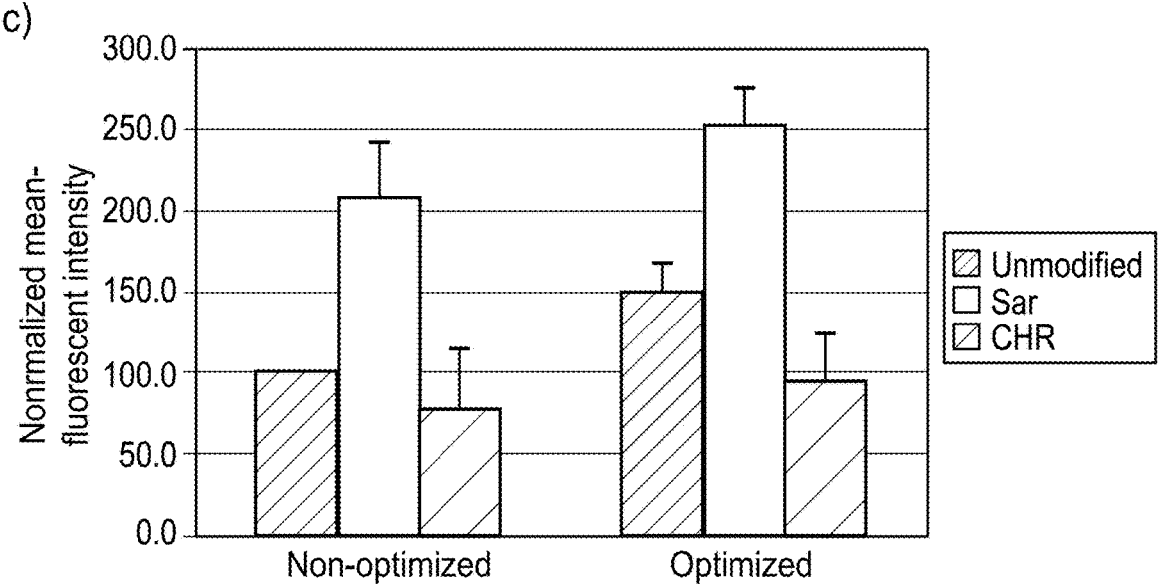

FIGURE 8
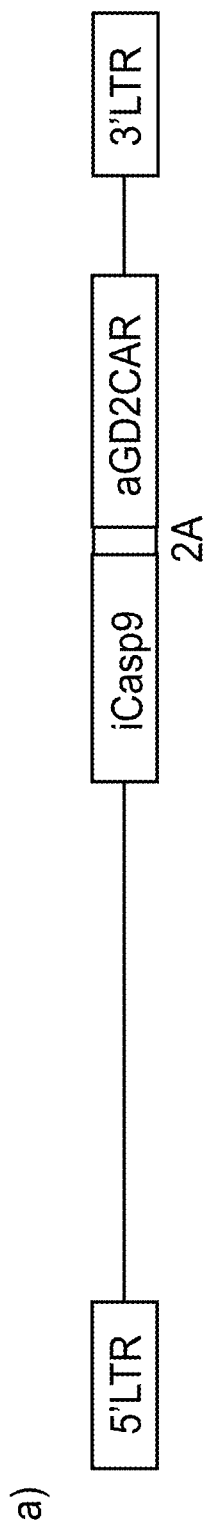
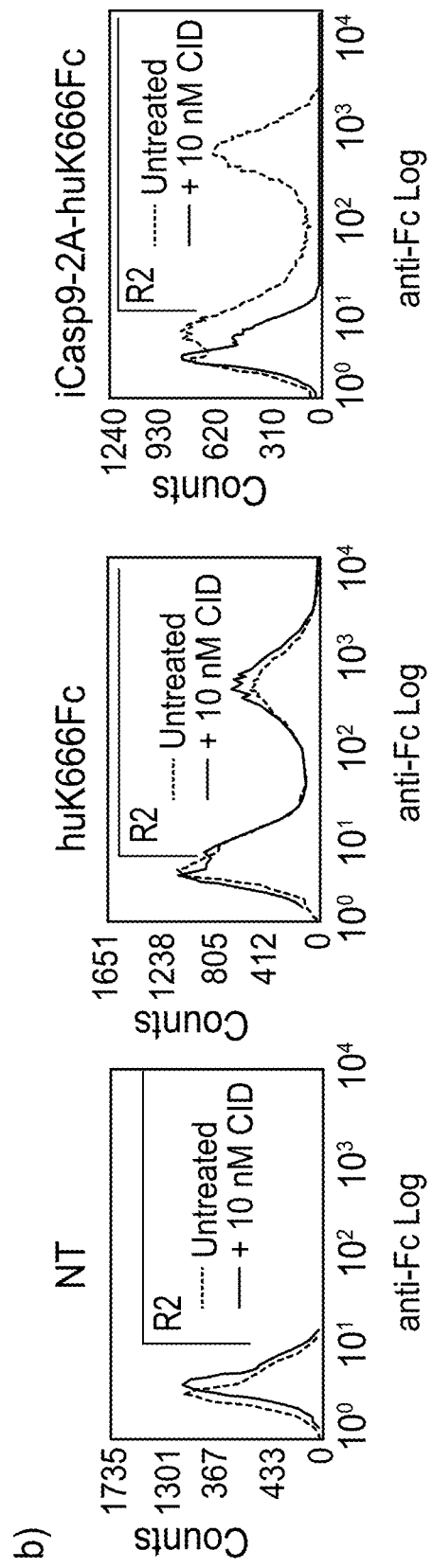

FIGURE 9
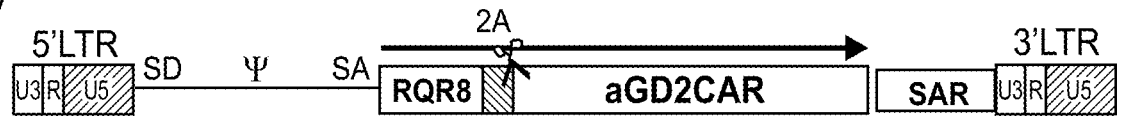
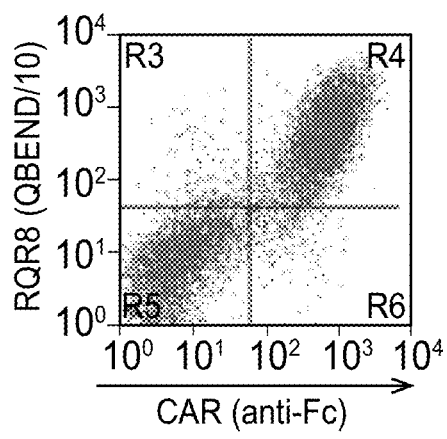
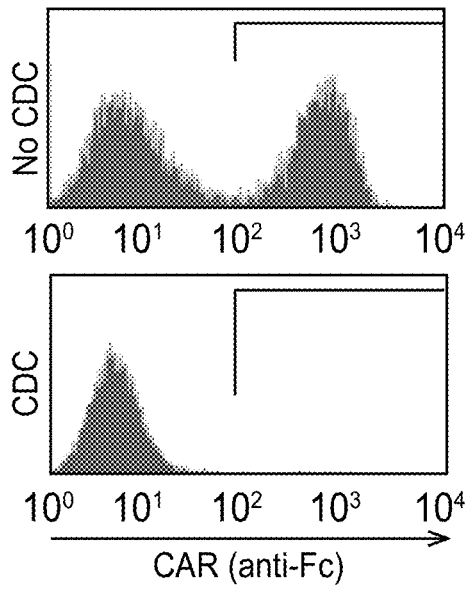
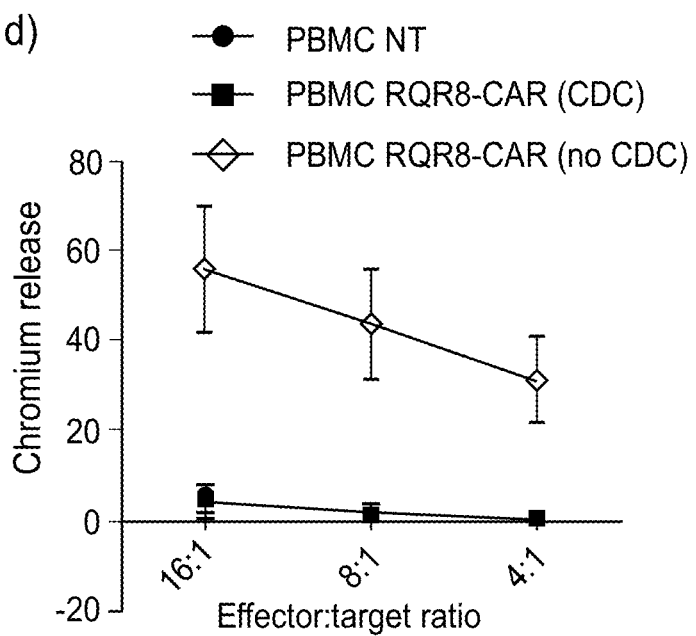

FIGURE 12

A.
METDTLLLWVLLLWVPGSTGQVQLKESGPVLVAPSQTLSITCTVSGFSLASYNIHWVRQPPGKGLEWLGVIWAGGS
TNYNSALMSRLSISKDNSKSQVFLQMNSLQTDDTAMYYCAKRSDDYSWFAYWGQGTLVTVSASGGGGSGGGGSGGG
GSENVLTQSPAIMSASPGEKVTMTCRASSSVSSYYLHWYQQKSGASPKVWIYSTSNLASGVPGRFSGSGSGTSYSL
TISSVEAEDAATYYCQQYSGYPITFGAGTKVEVKR*SDP*
*FWVLVVVGGVLACYSLLVTVAFIIFWV*
*KSRPLLHSDYMNMTPRRPGPTRKHYQPYAPPRDFAAYRSEDQRLPPDAHKPPGGGSFRTPIQEEQADAHSTLAKI*

B.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKRSDP
*FWVLVVVGGVLACYSLLVTVAFIIFWV*
*KSRPLLHSDYMNMTPRRPGPTRKHYQPYAPPRDFAAYRSEDQRLPPDAHKPPGGGSFRTPIQEEQADAHSTLAKI*

C.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKRSDP
*FWVLVVVGGVLACYSLLVTVAFIIFWV*
*RLLHSDYMNMTPRRPGPTRKHYQPYAPPRDFAAYRSEDQRLPPDAHKPPGGGSFRTPIQEEQADAHSTLAKI*

D.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKRSDP
*FWVLVVVGGVLACYSLLVTVAFIIFWV*KSRPLLHSDYMNMTPRRPGPTRKHYQPYAPPRDFAAYRSE
*DQRLPPDAHKPPGGGSFRTPIQEEQADAHSTLAKI*

E.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKRSDP
*FWVLVVVGGVLACYSLLVTVAFIIFWV*KSRPLLHSDYMNMTPRRPGPTRKHYQPYAPPRDFAAYRSE
*DQRLPPDAHKPPGGGSFRTPIQEEQADAHSTLAKI*

FIGURE 12 contd.

F.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKRSDP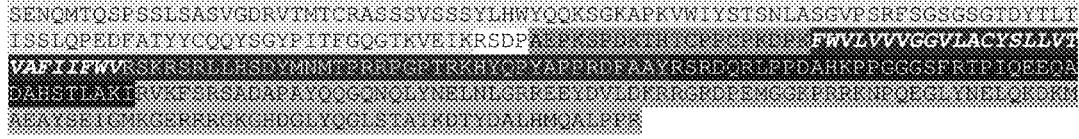
*FWVLVVVGGVLACYSLLVT*
*VAFIIFWV*SKRSRLLHSDYMNMTPRRPGPTRKHYQPYAPPRDFAAYRSRDQRLPPDAHKPPGGGSRTPIQEEDA
*DAHSTLAK*G G.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKRSDP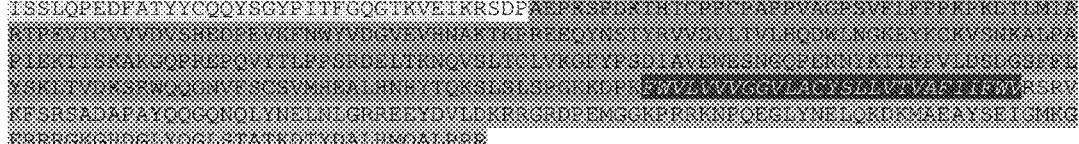

H.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKR*SDP*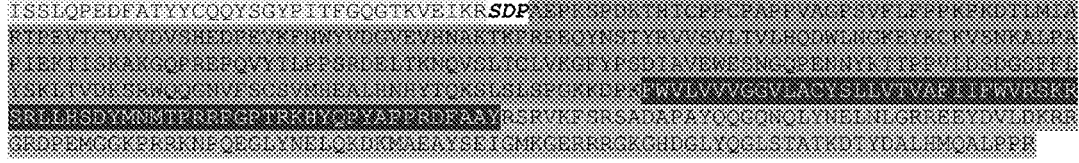

I.
METDTLLLWVLLLWVPGSTGQVQLQESGPGLVKP
SQTLSITCTVSGFSLASYNIHWVRQPPGKGLEWLGVIWAGGSTNYNSALMSRLTISKDNSKNQVFLKMSSLTAADT
AVYYCAKRSDDYSWFAYWGQGTLVTVSSGGGGSGGGGSGGGGSENQMTQSPSSLSASVGDRVTMTCRASSSVSSSY
LHWYQQKSGKAPKVWIYSTSNLASGVPSRFSGSGSGTDYTLTISSLQPEDFATYYCQQYSGYPITFGQGTKVEIKR
SDP

J.
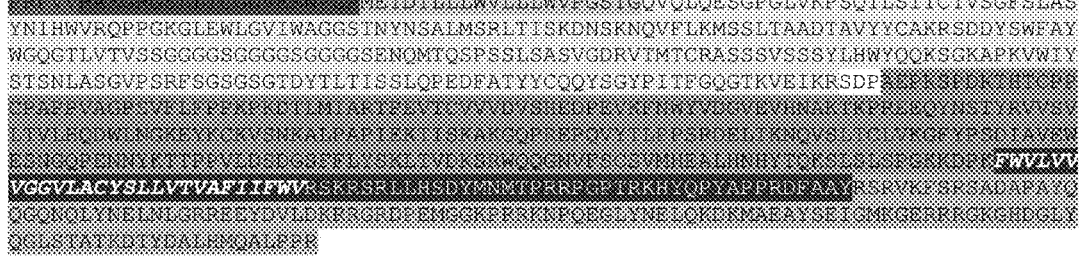METDTLLLWVLLLWVPGSTGQVQLQESGPGLVKPSQTLSITCTVSGFSLAS
YNIHWVRQPPGKGLEWLGVIWAGGSTNYNSALMSRLTISKDNSKNQVFLKMSSLTAADTAVYYCAKRSDDYSWFAY
WGQGTLVTVSSGGGGSGGGGSGGGGSENQMTQSPSSLSASVGDRVTMTCRASSSVSSSYLHWYQQKSGKAPKVWIY
STSNLASGVPSRFSGSGSGTDYTLTISSLQPEDFATYYCQQYSGYPITFGQGTKVEIKRSDP

FIGURE 12 contd.

| Region | Description |
|---|---|
| Suicide gene | Either iCasp9 or RQR8 |
| 2A | Foot-and-mouth disease 2A peptide |
| Signal | Signal peptide |
| scFv1 | scFv (either muKM666 or huKM666) |
| SDP | Linker and chain break |
| Spacer | CD8alpha stalk |
| CD28 TM | CD28 transmembrane domain |
| CD28 endo | CD28 endodomain |
| OX40 endo | OX40 endodomain |
| CD3Z endo | CD3 Zeta endodomain |

FIGURE 15
b) Lan 1 Alone
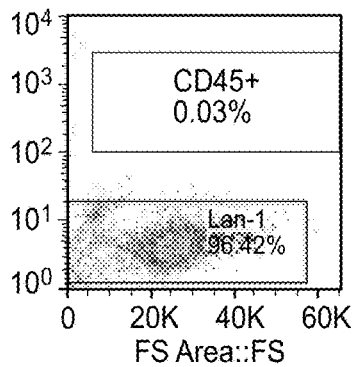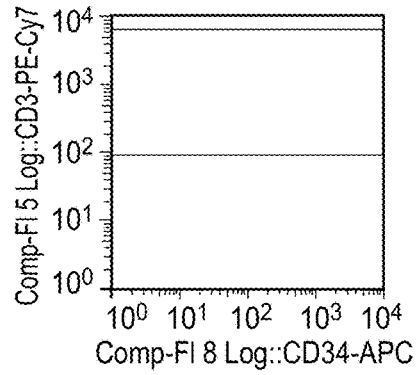
c) NT PBMCs+ Lan-1
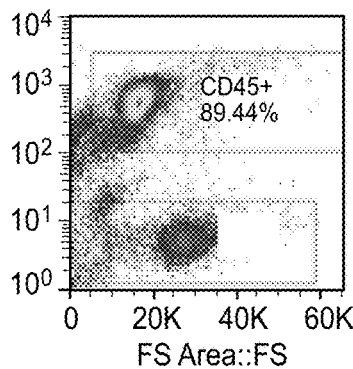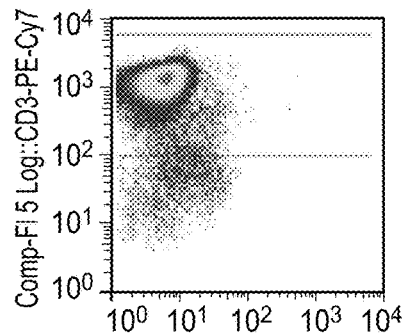
d) HuK-28Zeta+ Lan1
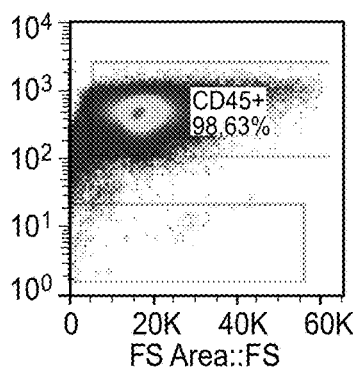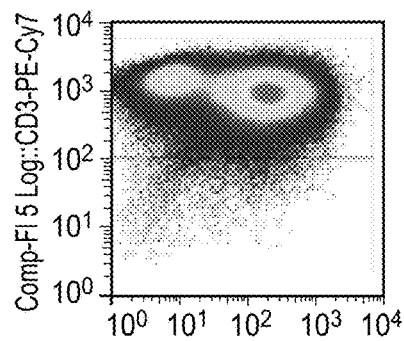
e) 14g2a-28Zeta+ Lan1v
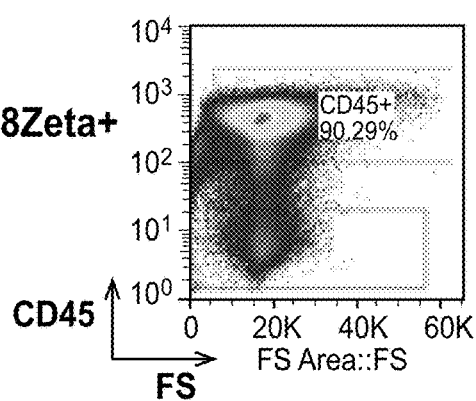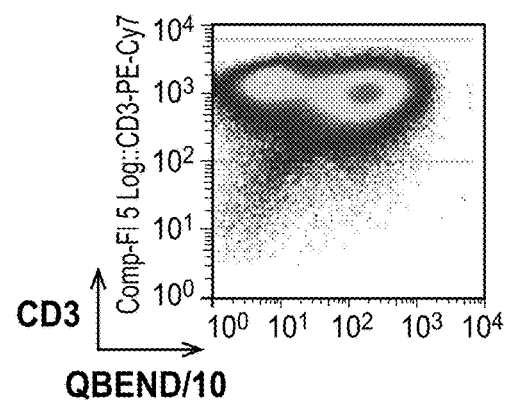

SEQUENCE LISTING

```
<160> NUMBER OF SEQ ID NOS: 37

<210> SEQ ID NO 1
<211> LENGTH: 5
<212> TYPE: PRT
<213> ORGANISM: Artificial Sequence
<220> FEATURE:
<223> OTHER INFORMATION: Heavy chain variable region CDR1

<400> SEQUENCE: 1

Ser Tyr Asn Ile His
1               5

<210> SEQ ID NO 2
<211> LENGTH: 16
<212> TYPE: PRT
<213> ORGANISM: Artificial Sequence
<220> FEATURE:
<223> OTHER INFORMATION: Heavy chain variable region CDR2

<400> SEQUENCE: 2

Val Ile Trp Ala Gly Gly Ser Thr Asn Tyr Asn Ser Ala Leu Met Ser
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Heavy chain variable region CDR3

<400> SEQUENCE: 3

Arg Ser Asp Asp Tyr Ser Trp Phe Ala Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Light chain variable region CDR1

<400> SEQUENCE: 4

Arg Ala Ser Ser Ser Val Ser Ser Ser Tyr Leu His
1               5                   10

<210> SEQ ID NO 5
<211> LENGTH: 7
<212> TYPE: PRT
```

-continued

```
<213> ORGANISM: Artificial Sequence
<220> FEATURE:
<223> OTHER INFORMATION: Light chain variable region CDR2

<400> SEQUENCE: 5

Ser Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Light chain variable region CDR3

<400> SEQUENCE: 6

Gln Gln Tyr Ser Gly Tyr Pro Ile Thr
1               5

<210> SEQ ID NO 7
<211> LENGTH: 243
<212> TYPE: PRT
<213> ORGANISM: Artificial Sequence
<220> FEATURE:
<223> OTHER INFORMATION: Murine KM666 sequence

<400> SEQUENCE: 7

Gln Val Gln Leu Lys Glu Ser Gly Pro Val Leu Val Ala Pro Ser Gln
1               5                   10                  15

Thr Leu Ser Ile Thr Cys Thr Val Ser Gly Phe Ser Leu Ala Ser Tyr
            20                  25                  30

Asn Ile His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Gln Met Asn Ser Leu Gln Thr Asp Asp Thr Ala Met Tyr Tyr Cys Ala
                85                  90                  95

Lys Arg Ser Asp Asp Tyr Ser Trp Phe Ala Tyr Trp Gly Gln Gly Thr
            100                 105                 110

Leu Val Thr Val Ser Ala Ser Gly Gly Gly Ser Gly Gly Gly Gly
        115                 120                 125

Ser Gly Gly Gly Gly Ser Glu Asn Val Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Ser Ser Tyr Leu His Trp Tyr Gln Gln Lys Ser Gly
                165                 170                 175

Ala Ser Pro Lys Val Trp Ile Tyr Ser Thr Ser Asn Leu Ala Ser Gly
            180                 185                 190

Val Pro Gly Arg Phe Ser Gly Ser Gly Ser Gly Thr Ser Tyr Ser Leu
        195                 200                 205

Thr Ile Ser Ser Val Glu Ala Glu Asp Ala Ala Thr Tyr Tyr Cys Gln
    210                 215                 220

Gln Tyr Ser Gly Tyr Pro Ile Thr Phe Gly Ala Gly Thr Lys Val Glu
225                 230                 235                 240

Val Lys Arg
```

<210> SEQ ID NO 8
<211> LENGTH: 242
<212> TYPE: PRT
<213> ORGANISM: Artificial Sequence
<220> FEATURE:
<223> OTHER INFORMATION: Humanised KM666 sequence

<400> SEQUENCE: 8

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Leu Ala Ser Tyr
            20                  25                  30

Asn Ile His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Thr Ile Ser Lys Asp Asn Ser Lys Asn Gln Val Phe Leu
65                  70                  75                  80

Lys Met Ser Ser Leu Thr Ala Ala Asp Thr Ala Val Tyr Tyr Cys Ala
                85                  90                  95

Lys Arg Ser Asp Asp Tyr Ser Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Asn Gln Met Thr Gln Ser Pro Ser Ser Leu
    130                 135                 140

Ser Ala Ser Val Gly Asp Arg Val Thr Met Thr Cys Arg Ala Ser Ser
145                 150                 155                 160

Ser Val Ser Ser Ser Tyr Leu His Trp Tyr Gln Gln Lys Ser Gly Lys
                165                 170                 175

Ala Pro Lys Val Trp Ile Tyr Ser Thr Ser Asn Leu Ala Ser Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Gln Gln
    210                 215                 220

Tyr Ser Gly Tyr Pro Ile Thr Phe Gly Gln Gly Thr Lys Val Glu Ile
225                 230                 235                 240

Lys Arg

<210> SEQ ID NO 9
<211> LENGTH: 118
<212> TYPE: PRT
<213> ORGANISM: Artificial Sequence
<220> FEATURE:
<223> OTHER INFORMATION: Murine KM666 VH (heavy chain variable region)
    sequence

<400> SEQUENCE: 9

Gln Val Gln Leu Lys Glu Ser Gly Pro Val Leu Val Ala Pro Ser Gln
1               5                   10                  15

Thr Leu Ser Ile Thr Cys Thr Val Ser Gly Phe Ser Leu Ala Ser Tyr
            20                  25                  30

Asn Ile His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

```
Ser Arg Leu Ser Ile Ser Lys Asp Asn Ser Lys Ser Gln Val Phe Leu
 65                  70                  75                  80

Gln Met Asn Ser Leu Gln Thr Asp Thr Ala Met Tyr Tyr Cys Ala
             85                  90                  95

Lys Arg Ser Asp Asp Tyr Ser Trp Phe Ala Tyr Trp Gly Gln Gly Thr
            100                 105                 110

Leu Val Thr Val Ser Ala
        115

<210> SEQ ID NO 10
<211> LENGTH: 118
<212> TYPE: PRT
<213> ORGANISM: Artificial Sequence
<220> FEATURE:
<223> OTHER INFORMATION: Humanised KM666 VH sequence

<400> SEQUENCE: 10

Gln Val Gln Leu Gln Glu Ser Gly Pro Gly Leu Val Lys Pro Ser Gln
  1               5                  10                  15

Thr Leu Ser Ile Thr Cys Thr Val Ser Gly Phe Ser Leu Ala Ser Tyr
             20                  25                  30

Asn Ile His Trp Val Arg Gln Pro Pro Gly Lys Gly Leu Glu Trp Leu
             35                  40                  45

Gly Val Ile Trp Ala Gly Gly Ser Thr Asn Tyr Asn Ser Ala Leu Met
 50                  55                  60

Ser Arg Leu Thr Ile Ser Lys Asp Asn Ser Lys Asn Gln Val Phe Leu
 65                  70                  75                  80

Lys Met Ser Ser Leu Thr Ala Ala Asp Thr Ala Val Tyr Tyr Cys Ala
             85                  90                  95

Lys Arg Ser Asp Asp Tyr Ser Trp Phe Ala Tyr Trp Gly Gln Gly Thr
            100                 105                 110

Leu Val Thr Val Ser Ser
        115

<210> SEQ ID NO 11
<211> LENGTH: 108
<212> TYPE: PRT
<213> ORGANISM: Artificial Sequence
<220> FEATURE:
<223> OTHER INFORMATION: Murine KM666 VL (light chain variable region)
      sequence

<400> SEQUENCE: 11

Glu Asn Val Leu Thr Gln Ser Pro Ala Ile Met Ser Ala Ser Pro Gly
  1               5                  10                  15

Glu Lys Val Thr Met Thr Cys Arg Ala Ser Ser Ser Val Ser Ser Ser
             20                  25                  30

Tyr Leu His Trp Tyr Gln Gln Lys Ser Gly Ala Ser Pro Lys Val Trp
             35                  40                  45

Ile Tyr Ser Thr Ser Asn Leu Ala Ser Gly Val Pro Gly Arg Phe Ser
 50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Pro
             85                  90                  95

Ile Thr Phe Gly Ala Gly Thr Lys Val Glu Val Lys
            100                 105
```

```
<210> SEQ ID NO 12
<211> LENGTH: 108
<212> TYPE: PRT
<213> ORGANISM: Artificial Sequence
<220> FEATURE:
<223> OTHER INFORMATION: Humanised KM666 VL sequence

<400> SEQUENCE: 12

Glu Asn Gln Met Thr Gln Ser Pro Ser Leu Ser Ala Ser Val Gly
1               5                   10                  15

Asp Arg Val Thr Met Thr Cys Arg Ala Ser Ser Ser Val Ser Ser
                20                  25                  30

Tyr Leu His Trp Tyr Gln Gln Lys Ser Gly Lys Ala Pro Lys Val Trp
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Tyr Ser Gly Tyr Pro
                85                  90                  95

Ile Thr Phe Gly Gln Gly Thr Lys Val Glu Ile Lys
            100                 105

<210> SEQ ID NO 13
<211> LENGTH: 27
<212> TYPE: PRT
<213> ORGANISM: Artificial Sequence
<220> FEATURE:
<223> OTHER INFORMATION: Transmembrane domain

<400> SEQUENCE: 13

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 14
<211> LENGTH: 39
<212> TYPE: PRT
<213> ORGANISM: Artificial Sequence
<220> FEATURE:
<223> OTHER INFORMATION: CD28 endodomain

<400> SEQUENCE: 14

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr
            35

<210> SEQ ID NO 15
<211> LENGTH: 38
<212> TYPE: PRT
<213> ORGANISM: Artificial Sequence
<220> FEATURE:
<223> OTHER INFORMATION: CD40 endodomain

<400> SEQUENCE: 15

Arg Ser Arg Asp Gln Arg Leu Pro Pro Asp Ala His Lys Pro Pro Gly
1               5                   10                  15
```

Gly Gly Ser Phe Arg Thr Pro Ile Gln Glu Glu Gln Ala Asp Ala His
        20                  25                  30

Ser Thr Leu Ala Lys Ile
        35

<210> SEQ ID NO 16
<211> LENGTH: 114
<212> TYPE: PRT
<213> ORGANISM: Artificial Sequence
<220> FEATURE:
<223> OTHER INFORMATION: CD3 zeta endodomain

<400> SEQUENCE: 16

Arg Ser Arg Val Lys Phe Ser Arg Ser Ala Asp Ala Pro Ala Tyr Gln
1               5                   10                  15

Gln Gly Gln Asn Gln Leu Tyr Asn Glu Leu Asn Leu Gly Arg Arg Glu
            20                  25                  30

Glu Tyr Asp Val Leu Asp Lys Arg Arg Gly Arg Asp Pro Glu Met Gly
        35                  40                  45

Gly Lys Pro Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg

<210> SEQ ID NO 17
<211> LENGTH: 153
<212> TYPE: PRT
<213> ORGANISM: Artificial Sequence
<220> FEATURE:
<223> OTHER INFORMATION: CD28Z

<400> SEQUENCE: 17

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Val Lys Phe Ser Arg Ser
        35                  40                  45

Ala Asp Ala Pro Ala Tyr Gln Gln Gly Gln Asn Gln Leu Tyr Asn Glu
    50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Arg Arg Lys Asn Pro Gln
                85                  90                  95

Glu Gly Leu Tyr Asn Glu Leu Gln Lys Asp Lys Met Ala Glu Ala Tyr
            100                 105                 110

Ser Glu Ile Gly Met Lys Gly Glu Arg Arg Arg Gly Lys Gly His Asp
        115                 120                 125

Gly Leu Tyr Gln Gly Leu Ser Thr Ala Thr Lys Asp Thr Tyr Asp Ala
    130                 135                 140

Leu His Met Gln Ala Leu Pro Pro Arg
145                 150

<210> SEQ ID NO 18
<211> LENGTH: 189
<212> TYPE: PRT
<213> ORGANISM: Artificial Sequence
<220> FEATURE:
<223> OTHER INFORMATION: CD28OXZ

<400> SEQUENCE: 18

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Asp Gln Arg Leu Pro Pro
        35                  40                  45

Asp Ala His Lys Pro Pro Gly Gly Gly Ser Phe Arg Thr Pro Ile Gln
    50                  55                  60

Glu Glu Gln Ala Asp Ala His Ser Thr Leu Ala Lys Ile Arg Val Lys
65                  70                  75                  80

Phe Ser Arg Ser Ala Asp Ala Pro Ala Tyr Gln Gln Gly Gln Asn Gln
                85                  90                  95

Leu Tyr Asn Glu Leu Asn Leu Gly Arg Arg Glu Glu Tyr Asp Val Leu
            100                 105                 110

Asp Lys Arg Arg Gly Arg Asp Pro Glu Met Gly Gly Lys Pro Arg Arg
        115                 120                 125

Lys Asn Pro Gln Glu Gly Leu Tyr Asn Glu Leu Gln Lys Asp Lys Met
    130                 135                 140

Ala Glu Ala Tyr Ser Glu Ile Gly Met Lys Gly Glu Arg Arg Arg Gly
145                 150                 155                 160

Lys Gly His Asp Gly Leu Tyr Gln Gly Leu Ser Thr Ala Thr Lys Asp
                165                 170                 175

Thr Tyr Asp Ala Leu His Met Gln Ala Leu Pro Pro Arg
            180                 185
```

<210> SEQ ID NO 19
<211> LENGTH: 20
<212> TYPE: PRT
<213> ORGANISM: Artificial Sequence
<220> FEATURE:
<223> OTHER INFORMATION: Signal peptide

<400> SEQUENCE: 19

```
Met Glu Thr Asp Thr Leu Leu Leu Trp Val Leu Leu Leu Trp Val Pro
1               5                   10                  15

Gly Ser Thr Gly
            20
```

<210> SEQ ID NO 20
<211> LENGTH: 234
<212> TYPE: PRT
<213> ORGANISM: Artificial Sequence
<220> FEATURE:
<223> OTHER INFORMATION: Hinge-CH2CH3 of human IgG1 spacer

<400> SEQUENCE: 20

```
Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
```

```
                 35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Lys Lys Asp
225                 230

<210> SEQ ID NO 21
<211> LENGTH: 46
<212> TYPE: PRT
<213> ORGANISM: Artificial Sequence
<220> FEATURE:
<223> OTHER INFORMATION: Human CD8 stalk spacer

<400> SEQUENCE: 21

Thr Thr Thr Pro Ala Pro Arg Pro Pro Thr Pro Ala Pro Thr Ile Ala
 1               5                  10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
                35                  40                  45

<210> SEQ ID NO 22
<211> LENGTH: 20
<212> TYPE: PRT
<213> ORGANISM: Artificial Sequence
<220> FEATURE:
<223> OTHER INFORMATION: Human IgG1 hinge spacer

<400> SEQUENCE: 22

Ala Glu Pro Lys Ser Pro Asp Lys Thr His Thr Cys Pro Pro Cys Pro
 1               5                  10                  15

Lys Asp Pro Lys
                20

<210> SEQ ID NO 23
<211> LENGTH: 237
<212> TYPE: PRT
<213> ORGANISM: Artificial Sequence
<220> FEATURE:
```

<223> OTHER INFORMATION: IgG1 Hinge-Fc spacer

<400> SEQUENCE: 23

Ala Glu Pro Lys Ser Pro Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Lys Asp Pro Lys
225                 230                 235

<210> SEQ ID NO 24
<211> LENGTH: 236
<212> TYPE: PRT
<213> ORGANISM: Artificial Sequence
<220> FEATURE:
<223> OTHER INFORMATION: IgG1 Hinge spacer - Fc modified to remove Fc
      receptor recognition motifs

<400> SEQUENCE: 24

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala

```
                      100                 105                 110
Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp Pro Lys
225                 230                 235

<210> SEQ ID NO 25
<211> LENGTH: 6014
<212> TYPE: DNA
<213> ORGANISM: Artificial Sequence
<220> FEATURE:
<223> OTHER INFORMATION: Retroviral cassette

<400> SEQUENCE: 25
tgaaagaccc cacctgtagg tttggcaagc tagcttaagt aacgccattt tgcaaggcat      60
ggaaaaatac ataactgaga atagaaaagt tcagatcaag gtcaggaaca gatggaacag     120
ctgaatatgg gccaaacagg atatctgtgg taagcagttc ctgccccggc tcagggccaa     180
gaacagatgg aacagctgaa tatgggccaa acaggatatc tgtggtaagc agttcctgcc     240
ccggctcagg gccaagaaca tggtccccag atgcggtcca gccctcagca gtttctagag     300
agaaccatca gatgtttcca gggtgcccca aggacctgaa atgaccctgt gccttatttg     360
aactaaccaa tcagttcgct tctcgcttct gttcgcgcgc ttatgctccc cgagctcaat     420
aaaagagccc acaacccctc actcggggcg ccagtcctcc gattgactga gtcgcccggg     480
tacccgtgta tccaataaac cctcttgcag ttgcatccga cttgtggtct cgctgttcct     540
tgggagggtc tcctctgagt gattgactac ccgtcagcgg ggtctttca tttgggggct     600 cgtccgggat cggagaccc ctgcccaggg accaccgacc caccaccggg aggtaagctg     660
gccagcaact tatctgtgtc tgtccgattg tctagtgtct atgactgatt ttatgcgcct     720
gcgtcggtac tagttagcta actagctctg tatctggcgg acccgtggtg gaactgacga     780
gttcggaaca cccggccgca accctgggag acgtcccagg gacttcgggg gccgttttttg    840 tggcccgacc tgagtcctaa atcccgatc gtttaggact cttttggtgca ccccccttag     900 aggagggata tgtggttctg gtaggagacg agaacctaaa acagttcccg cctccgtctg     960 aattttttgct ttcggtttgg gaccgaagcc gcgccgcgcg tcttgtctgc tgcagcatcg    1020
ttctgtgttg tctctgtctg actgtgtttc tgtatttgtc tgaaaatatg ggcccgggct    1080
agcctgttac cactccctta agtttgacct taggtcactg gaaagatgtc gagcggatcg    1140
ctcacaacca gtcggtagat gtcaagaaga gacgttgggt taccttctgc tctgcagaat    1200
ggccaacctt taacgtcgga tggccgcgag acggcacctt taaccgagac ctcatcaccc    1260
aggttaagat caaggtcttt tcacctggcc cgcatggaca cccagaccag gtggggtaca    1320
```

```
tcgtgacctg ggaagccttg gcttttgacc cccctccctg ggtcaagccc tttgtacacc   1380
ctaagcctcc gcctcctctt cctccatccg ccccgtctct ccccccttgaa cctcctcgtt   1440
cgacccccgcc tcgatcctcc ctttatccag ccctcactcc ttctctaggc gcccccatat   1500
ggccatatga gatcttatat ggggcacccc cgccccttgt aaacttccct gaccctgaca   1560
tgacaagagt tactaacagc ccctctctcc aagctcactt acaggctctc tacttagtcc   1620
agcacgaagt ctggagacct ctggcggcag cctaccaaga caactggac cgaccggtgg     1680
tacctcaccc ttaccgagtc ggcgacacag tgtgggtccg ccgacaccag actaagaacc    1740
tagaacctcg ctggaaagga ccttacacag tcctgctgac cacccccacc gccctcaaag    1800
tagacggcat cgcagcttgg atacacgccg cccacgtgaa ggctgccgac cccggggtg     1860
gaccatcctc tagactgcca acatgggcac cagcctgctg tgctggatgg ccctgtgcct    1920
gctgggcgcc gaccacgccg atgcctgccc ctacagcaac cccagcctgt gcagcggagg    1980
cggcggcagc gagctgccca cccagggcac cttctccaac gtgtccacca acgtgagccc    2040
agccaagccc accaccaccg cctgtcctta ttccaatcct tccctgtgta gcggaggggg    2100
aggcagccca gccccagac ctcccacccc agccccacc atcgccagcc agcctctgag      2160
cctgagaccc gaggcctgcc gccagccgc cggcggcgcc gtgcacacca gaggcctgga    2220
tttcgcctgc gatatctaca tctgggcccc actggccggc acctgtggcg tgctgctgct   2280
gagcctggtg atcaccctgt actgcaacca ccgcaaccgc aggcgcgtgt gcaagtgccc   2340
caggcccgtg gtgagagccg agggcagagg cagcctgctg acctgcggcg acgtggagga   2400
gaacccaggc cccatggaga ccgacaccct gctgctgtgg gtgctgctgc tgtgggtgcc   2460
aggcagcacc ggccaggtgc agctgcagga gtctggccca ggcctggtga agcccagcca   2520
gaccctgagc atcacctgca ccgtgagcgg cttcagcctg gccagctaca acatccactg   2580
ggtgcggcag ccccaggca agggcctgga gtggctgggc gtgatctggg ctggcggcag   2640
caccaactac aacagcgccc tgatgagccg gctgaccatc agcaaggaca cagcaagaa    2700
ccaggtgttc ctgaagatga gcagcctgac agccgccgac accgccgtgt actactgcgc   2760
caagcggagc gacgactaca gctggttcgc ctactgggc cagggcaccc tggtgaccgt    2820
gagctctggc ggaggcggct ctggcggagg cggctctggc ggaggcggca gcgagaacca   2880
gatgacccag agcccagca gcttgagcgc cagcgtgggc gaccgggtga ccatgacctg    2940
cagagccagc agcagcgtga gcagcagcta cctgcactgg taccagcaga gagcggcaa    3000
ggcccccaaag gtgtggatct acagcaccag caacctggcc agcggcgtgc cagccggtt    3060
cagcggcagc ggcagcggca ccgactacac cctgaccatc agcagcctgc agcccgagga   3120
cttcgccacc tactactgcc agcagtacag cggctacccc atcaccttcg gccagggcac   3180
caaggtggag atcaagcggt cggatcccgc cgagcccaaa tctcctgaca aaactcacac   3240
atgcccaccg tgcccagcac ctcccgtggc cggcccgtca gtcttcctct tccccccaaa   3300
acccaaggac accctcatga tcgcccggac ccctgaggtc acatgcgtgg tggtggacgt   3360
gagccacgaa gaccctgagg tcaagttcaa ctggtacgtg gacggcgtgg aggtgcataa   3420
tgccaagaca aagccgcggg aggagcagta caacagcacg taccgtgtgg tcagcgtcct   3480
caccgtcctg caccaggact ggctgaatgg caaggagtac aagtgcaagg tctccaacaa   3540
agccctccca gcccccatcg agaaaaccat ctccaaagcc aaagggcagc ccgagaacc    3600
acaggtgtac accctgcccc catcccggga tgagctgacc aagaaccagg tcagcctgac   3660
```

-continued

```
ctgcctggtc aaaggcttct atcccagcga catcgccgtg gagtgggaga gcaatgggca      3720
accggagaac aactacaaga ccacgcctcc cgtgctggac tccgacggct ccttcttcct      3780
ctacagcaag ctcaccgtgg acaagagcag gtggcagcag gggaacgtct tctcatgctc      3840
cgtgatgcat gaggccctgc acaatcacta tacccagaaa tctctgagtc tgagcccagg      3900
caagaaggac cccaagttct gggtcctggt ggtggtggga ggcgtgctgg cctgttactc      3960
tctcctggtg accgtggcct tcatcatctt ctgggtgcgc tccaagagga gcaggctcct      4020
gcacagtgac tacatgaaca tgactccccg ccgccccggg cccacccgca agcattacca      4080
gcccctatgcc ccaccacgcg acttcgcagc ctatcgctcc cgggtgaagt tctctcgctc      4140
tgccgatgcc ccagcctatc agcagggcca gaatcagctg tacaatgaac tgaacctggg      4200
caggcgggag gagtacgacg tgctggataa gcggagaggc agagaccccg agatgggcgg      4260
caaaccacgg cgcaaaaatc cccaggaggg actctataac gagctgcaga aggacaaaat      4320
ggccgaggcc tattccgaga tcggcatgaa gggagagaga agacgcggaa agggccacga      4380
cggcctgtat cagggattgt ccaccgctac aaaagataca tatgatgccc tgcacatgca      4440
ggcccctgcca cccagatgac gcgtatcgat actgttctca tcacatcata tcaaggttat      4500
ataccatcaa tattgccaca gatgttactt agccttttaa tatttctcta atttagtgta      4560
tatgcaatga tagttctctg atttctgaga ttgagtttct catgtgtaat gattatttag      4620
agtttctctt tcatctgttc aaattttgt ctagttttat ttttactga tttgtaagac       4680
ttcttttat aatctgcata ttacaattct ctttactggg gtgttgcaaa tatttctgt       4740
cattctatgg cctgactttt cttaatggtt ttttaatttt aaaaataagt cttaatattc      4800
atgcaatcta attaacaatc ttttctttgt ggttaggact ttgagtcata agaaatttt       4860
ctctacactg aagtcatgat ggcatgcttc tatattattt tctaaaagat ttaaagttt       4920
gccttctcca tttagactta taattcactg gaattttttt gtgtgtatgg tatgacatat      4980
gggttccctt ttattttta catataaata tatttccctg tttttctaaa aagaaaaag       5040
atcatcattt tcccattgta aaatgccata ttttttcat aggtcactta catatatcaa      5100
tgggtctgtt tctgagctct actctatttt atcagcctca ctgtctatcc ccacacatct      5160
catgctttgc tctaaatctt gatattagt ggaacattct ttcccatttt gttctacaag      5220
aatattttg ttattgtctt tgggctttct atatacattt tgaaatgagg ttgacaagtt      5280
cggattagtc caatttgtta aagacaggat atcagtggtc caggctctag ttttgactca      5340
acaatatcac cagctgaagc ctatagagta cgagccatag ataaaataaa agatttttatt     5400
tagtctccag aaaaagggg gaatgaaaga ccccaccgt aggtttggca agctagctta        5460
agtaacgcca ttttgcaagg catggaaaaa tacataactg agaatagaga agttcagatc      5520
aaggtcagga acagatggaa cagctgaata tgggccaaac aggatatctg tggtaagcag      5580
ttcctgcccc ggctcaggc caagaacaga tggaacagct gaatatgggc caaacaggat       5640
atctgtggta agcagttcct gccccggctc agggccaaga acagatggtc cccagatgcg      5700
gtccagccct cagcagtttc tagagaacca tcagatgttt ccagggtgcc caaggacct      5760
gaaatgaccc tgtgccttat ttgaactaac caatcagttc gcttctcgct tctgttcgcg      5820
cgcttctgct ccccgagctc aataaaagag cccacaaccc ctcactcggg gcgccagtcc      5880
tccgattgac tgagtcgccc gggtacccgt gtatccaata aaccctcttg cagttgcatc      5940
cgacttgtgg tctcgctgtt ccttgggagg gtctcctctg agtgattgac tacccgtcag      6000
cgggggtctt tcac                                                       6014
```

<210> SEQ ID NO 26
<211> LENGTH: 719
<212> TYPE: PRT
<213> ORGANISM: Artificial Sequence
<220> FEATURE:
<223> OTHER INFORMATION: anti-GD2 CAR, muKM666-HCH2CH3-CD28OXZ

<400> SEQUENCE: 26

```
Met Glu Thr Asp Thr Leu Leu Leu Trp Val Leu Leu Leu Trp Val Pro
1               5                   10                  15

Gly Ser Thr Gly Gln Val Gln Leu Lys Glu Ser Gly Pro Val Leu Val
            20                  25                  30

Ala Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Ser Ile Ser Lys Asp Asn Ser Lys Ser
                85                  90                  95

Gln Val Phe Leu Gln Met Asn Ser Leu Gln Thr Asp Asp Thr Ala Met
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ala Ser Gly Gly Gly Gly Ser
    130                 135                 140

Gly Gly Gly Gly Ser Gly Gly Gly Ser Glu Asn Val Leu Thr Gln
145                 150                 155                 160

Ser Pro Ala Ile Met Ser Ala Ser Pro Gly Glu Lys Val Thr Met Thr
                165                 170                 175

Cys Arg Ala Ser Ser Ser Val Ser Ser Ser Tyr Leu His Trp Tyr Gln
            180                 185                 190

Gln Lys Ser Gly Ala Ser Pro Lys Val Trp Ile Tyr Ser Thr Ser Asn
        195                 200                 205

Leu Ala Ser Gly Val Pro Gly Arg Phe Ser Gly Ser Gly Ser Gly Thr
    210                 215                 220

Ser Tyr Ser Leu Thr Ile Ser Ser Val Glu Ala Glu Asp Ala Ala Thr
225                 230                 235                 240

Tyr Tyr Cys Gln Gln Tyr Ser Gly Tyr Pro Ile Thr Phe Gly Ala Gly
                245                 250                 255

Thr Lys Val Glu Val Lys Arg Ser Asp Pro Ala Glu Pro Lys Ser Pro
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365
```

```
Lys Glu Tyr Lys Cys Lys Val Ser Asn Lys Ala Leu Pro Ala Pro Ile
            370             375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
                405                 410                 415
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
                435                 440                 445
Val Leu Asp Ser Asp Gly Ser Phe Phe Leu Tyr Ser Lys Leu Thr Val
450                 455                 460
Asp Lys Ser Arg Trp Gln Gln Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Pro Gly Lys Lys Asp Pro Lys Phe Trp Val Leu Val Val Val Gly Gly
            500                 505                 510
Val Leu Ala Cys Tyr Ser Leu Leu Val Thr Val Ala Phe Ile Ile Phe
            515                 520                 525
Trp Val Arg Ser Lys Arg Ser Arg Leu Leu His Ser Asp Tyr Met Asn
530                 535                 540
Met Thr Pro Arg Arg Pro Gly Pro Thr Arg Lys His Tyr Gln Pro Tyr
545                 550                 555                 560
Ala Pro Pro Arg Asp Phe Ala Ala Tyr Arg Ser Arg Asp Gln Arg Leu
                565                 570                 575
Pro Pro Asp Ala His Lys Pro Gly Gly Gly Ser Phe Arg Thr Pro
            580                 585                 590
Ile Gln Glu Glu Gln Ala Asp Ala His Ser Thr Leu Ala Lys Ile Arg
                595                 600                 605
Val Lys Phe Ser Arg Ser Ala Asp Ala Pro Ala Tyr Gln Gln Gly Gln
            610                 615                 620
Asn Gln Leu Tyr Asn Glu Leu Asn Leu Gly Arg Arg Glu Glu Tyr Asp
625                 630                 635                 640
Val Leu Asp Lys Arg Arg Gly Arg Asp Pro Glu Met Gly Gly Lys Pro
                645                 650                 655
Arg Arg Lys Asn Pro Gln Glu Gly Leu Tyr Asn Glu Leu Gln Lys Asp
            660                 665                 670
Lys Met Ala Glu Ala Tyr Ser Glu Ile Gly Met Lys Gly Glu Arg Arg
            675                 680                 685
Arg Gly Lys Gly His Asp Gly Leu Tyr Gln Gly Leu Ser Thr Ala Thr
            690                 695                 700
Lys Asp Thr Tyr Asp Ala Leu His Met Gln Ala Leu Pro Pro Arg
705                 710                 715

<210> SEQ ID NO 27
<211> LENGTH: 718
<212> TYPE: PRT
<213> ORGANISM: Artificial Sequence
<220> FEATURE:
<223> OTHER INFORMATION: anti-GD2 CAR, huKM666-HCH2CH3-CD28OXZ

<400> SEQUENCE: 27

Met Glu Thr Asp Thr Leu Leu Leu Trp Val Leu Leu Leu Trp Val Pro
1               5                   10                  15
```

-continued

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
            35                  40                  45

Leu Ala Ser Tyr Asn Ile His Trp Val Arg Gln Pro Pro Gly Lys Gly
50                      55                  60

Leu Glu Trp Leu Gly Val Ile Trp Ala Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
            115                 120                 125

Gly Gln Gly Thr Leu Val Thr Val Ser Ser Gly Gly Gly Ser Gly
            130                 135                 140

Gly Gly Gly Ser Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190

Lys Ser Gly Lys Ala Pro Lys Val Trp Ile Tyr Ser Thr Ser Asn Leu
            195                 200                 205

Ala Ser Gly Val Pro Ser Arg Phe Ser Gly Ser Gly Ser Gly Thr Asp
            210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
            245                 250                 255

Lys Val Glu Ile Lys Arg Ser Asp Pro Ala Glu Pro Lys Ser Pro Asp
            260                 265                 270

Lys Thr His Thr Cys Pro Pro Cys Pro Ala Pro Glu Leu Leu Gly Gly
            275                 280                 285

Pro Ser Val Phe Leu Phe Pro Pro Lys Pro Lys Asp Thr Leu Met Ile
            290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
            355                 360                 365

Glu Tyr Lys Cys Lys Val Ser Asn Lys Ala Leu Pro Ala Pro Ile Glu
            370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
            420                 425                 430

```
Glu Ser Asn Gly Gln Pro Glu Asn Asn Tyr Lys Thr Thr Pro Pro Val
            435                 440                 445

Leu Asp Ser Asp Gly Ser Phe Phe Leu Tyr Ser Lys Leu Thr Val Asp
        450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Lys Asp Pro Lys Phe Trp Val Leu Val Val Val Gly Gly Val
                500                 505                 510

Leu Ala Cys Tyr Ser Leu Leu Val Thr Val Ala Phe Ile Ile Phe Trp
        515                 520                 525

Val Arg Ser Lys Arg Ser Arg Leu Leu His Ser Asp Tyr Met Asn Met
530                 535                 540

Thr Pro Arg Arg Pro Gly Pro Thr Arg Lys His Tyr Gln Pro Tyr Ala
545                 550                 555                 560

Pro Pro Arg Asp Phe Ala Ala Tyr Arg Ser Arg Asp Gln Arg Leu Pro
                565                 570                 575

Pro Asp Ala His Lys Pro Pro Gly Gly Gly Ser Phe Arg Thr Pro Ile
                580                 585                 590

Gln Glu Glu Gln Ala Asp Ala His Ser Thr Leu Ala Lys Ile Arg Val
                595                 600                 605

Lys Phe Ser Arg Ser Ala Asp Ala Pro Ala Tyr Gln Gln Gly Gln Asn
        610                 615                 620

Gln Leu Tyr Asn Glu Leu Asn Leu Gly Arg Arg Glu Glu Tyr Asp Val
625                 630                 635                 640

Leu Asp Lys Arg Arg Gly Arg Asp Pro Glu Met Gly Gly Lys Pro Arg
                645                 650                 655

Arg Lys Asn Pro Gln Glu Gly Leu Tyr Asn Glu Leu Gln Lys Asp Lys
                660                 665                 670

Met Ala Glu Ala Tyr Ser Glu Ile Gly Met Lys Gly Glu Arg Arg Arg
                675                 680                 685

Gly Lys Gly His Asp Gly Leu Tyr Gln Gly Leu Ser Thr Ala Thr Lys
        690                 695                 700

Asp Thr Tyr Asp Ala Leu His Met Gln Ala Leu Pro Pro Arg
705                 710                 715

<210> SEQ ID NO 28
<211> LENGTH: 717
<212> TYPE: PRT
<213> ORGANISM: Artificial Sequence
<220> FEATURE:
<223> OTHER INFORMATION: anti-GD2 CAR, huKM666-HCH2CH3pvaa-CD28OXZ

<400> SEQUENCE: 28

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80
```

```
Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
            115                 120                 125

Gly Gln Gly Thr Leu Val Thr Val Ser Ser Gly Gly Gly Gly Ser Gly
            130                 135                 140

Gly Gly Gly Ser Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
                180                 185                 190

Lys Ser Gly Lys Ala Pro Lys Val Trp Ile Tyr Ser Thr Ser Asn Leu
                195                 200                 205

Ala Ser Gly Val Pro Ser Arg Phe Ser Gly Ser Gly Ser Gly Thr Asp
210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
            245                 250                 255

Lys Val Glu Ile Lys Arg Ser Asp Pro Ala Glu Pro Lys Ser Pro Asp
                260                 265                 270

Lys Thr His Thr Cys Pro Pro Cys Pro Ala Pro Val Ala Gly Pro
                275                 280                 285

Ser Val Phe Leu Phe Pro Pro Lys Pro Lys Asp Thr Leu Met Ile Ala
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
```

```
                    500                 505                 510
Ala Cys Tyr Ser Leu Leu Val Thr Val Ala Phe Ile Ile Phe Trp Val
            515                 520                 525

Arg Ser Lys Arg Ser Arg Leu Leu His Ser Asp Tyr Met Asn Met Thr
            530                 535                 540

Pro Arg Arg Pro Gly Pro Thr Arg Lys His Tyr Gln Pro Tyr Ala Pro
545                 550                 555                 560

Pro Arg Asp Phe Ala Ala Tyr Arg Ser Arg Asp Gln Arg Leu Pro Pro
                565                 570                 575

Asp Ala His Lys Pro Pro Gly Gly Gly Ser Phe Arg Thr Pro Ile Gln
            580                 585                 590

Glu Glu Gln Ala Asp Ala His Ser Thr Leu Ala Lys Ile Arg Val Lys
            595                 600                 605

Phe Ser Arg Ser Ala Asp Ala Pro Ala Tyr Gln Gln Gly Gln Asn Gln
            610                 615                 620

Leu Tyr Asn Glu Leu Asn Leu Gly Arg Arg Glu Glu Tyr Asp Val Leu
625                 630                 635                 640

Asp Lys Arg Arg Gly Arg Asp Pro Glu Met Gly Gly Lys Pro Arg Arg
                645                 650                 655

Lys Asn Pro Gln Glu Gly Leu Tyr Asn Glu Leu Gln Lys Asp Lys Met
            660                 665                 670

Ala Glu Ala Tyr Ser Glu Ile Gly Met Lys Gly Glu Arg Arg Arg Gly
            675                 680                 685

Lys Gly His Asp Gly Leu Tyr Gln Gly Leu Ser Thr Ala Thr Lys Asp
            690                 695                 700

Thr Tyr Asp Ala Leu His Met Gln Ala Leu Pro Pro Arg
705                 710                 715

<210> SEQ ID NO 29
<211> LENGTH: 527
<212> TYPE: PRT
<213> ORGANISM: Artificial Sequence
<220> FEATURE:
<223> OTHER INFORMATION: anti-GD2 CAR, huKM666-HSTK-CD28OXZ

<400> SEQUENCE: 29

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Asn Gln Met Thr Gln Ser
```

```
145                 150                 155                 160
Pro Ser Ser Leu Ser Ala Ser Val Gly Asp Arg Val Thr Met Thr Cys
                165                 170                 175
Arg Ala Ser Ser Val Ser Ser Tyr Leu His Trp Tyr Gln Gln
            180                 185                 190
Lys Ser Gly Lys Ala Pro Lys Val Trp Ile Tyr Ser Thr Ser Asn Leu
            195                 200                 205
Ala Ser Gly Val Pro Ser Arg Phe Ser Gly Ser Gly Ser Gly Thr Asp
    210                 215                 220
Tyr Thr Leu Thr Ile Ser Ser Leu Gln Pro Glu Asp Phe Ala Thr Tyr
225                 230                 235                 240
Tyr Cys Gln Gln Tyr Ser Gly Tyr Pro Ile Thr Phe Gly Gln Gly Thr
                245                 250                 255
Lys Val Glu Ile Lys Arg Ser Asp Pro Thr Thr Thr Pro Ala Pro Arg
            260                 265                 270
Pro Pro Thr Pro Ala Pro Thr Ile Ala Ser Gln Pro Leu Ser Leu Arg
            275                 280                 285
Pro Glu Ala Cys Arg Pro Ala Ala Gly Gly Ala Val His Thr Arg Gly
    290                 295                 300
Leu Asp Phe Ala Cys Asp Ile Phe Trp Val Leu Val Val Val Gly Gly
305                 310                 315                 320
Val Leu Ala Cys Tyr Ser Leu Leu Val Thr Val Ala Phe Ile Ile Phe
                325                 330                 335
Trp Val Arg Ser Lys Arg Ser Arg Leu Leu His Ser Asp Tyr Met Asn
            340                 345                 350
Met Thr Pro Arg Arg Pro Gly Pro Thr Arg Lys His Tyr Gln Pro Tyr
            355                 360                 365
Ala Pro Pro Arg Asp Phe Ala Ala Tyr Arg Ser Arg Asp Gln Arg Leu
    370                 375                 380
Pro Pro Asp Ala His Lys Pro Pro Gly Gly Gly Ser Phe Arg Thr Pro
385                 390                 395                 400
Ile Gln Glu Glu Gln Ala Asp Ala His Ser Thr Leu Ala Lys Ile Arg
                405                 410                 415
Val Lys Phe Ser Arg Ser Ala Asp Ala Pro Ala Tyr Gln Gln Gly Gln
            420                 425                 430
Asn Gln Leu Tyr Asn Glu Leu Asn Leu Gly Arg Arg Glu Glu Tyr Asp
            435                 440                 445
Val Leu Asp Lys Arg Arg Gly Arg Asp Pro Glu Met Gly Gly Lys Pro
    450                 455                 460
Arg Arg Lys Asn Pro Gln Glu Gly Leu Tyr Asn Glu Leu Gln Lys Asp
465                 470                 475                 480
Lys Met Ala Glu Ala Tyr Ser Glu Ile Gly Met Lys Gly Glu Arg Arg
                485                 490                 495
Arg Gly Lys Gly His Asp Gly Leu Tyr Gln Gly Leu Ser Thr Ala Thr
            500                 505                 510
Lys Asp Thr Tyr Asp Ala Leu His Met Gln Ala Leu Pro Pro Arg
            515                 520                 525

<210> SEQ ID NO 30
<211> LENGTH: 527
<212> TYPE: PRT
<213> ORGANISM: Artificial Sequence
<220> FEATURE:
<223> OTHER INFORMATION: anti-GD2 CAR, huKM666-STK-CD28XOXZ
```

<400> SEQUENCE: 30

```
Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190

Lys Ser Gly Lys Ala Pro Lys Val Trp Ile Tyr Ser Thr Ser Asn Leu
        195                 200                 205

Ala Ser Gly Val Pro Ser Arg Phe Ser Gly Ser Gly Ser Gly Thr Asp
    210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
                245                 250                 255

Lys Val Glu Ile Lys Arg Ser Asp Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr
        355                 360                 365

Ala Pro Pro Arg Asp Phe Ala Ala Tyr Arg Ser Arg Asp Gln Arg Leu
    370                 375                 380

Pro Pro Asp Ala His Lys Pro Pro Gly Gly Gly Ser Phe Arg Thr Pro
385                 390                 395                 400

Ile Gln Glu Glu Gln Ala Asp Ala His Ser Thr Leu Ala Lys Ile Arg
                405                 410                 415
```

-continued

```
Val Lys Phe Ser Arg Ser Ala Asp Ala Pro Ala Tyr Gln Gln Gly Gln
            420                 425                 430

Asn Gln Leu Tyr Asn Glu Leu Asn Leu Gly Arg Arg Glu Glu Tyr Asp
            435                 440                 445

Val Leu Asp Lys Arg Arg Gly Arg Asp Pro Glu Met Gly Gly Lys Pro
450                 455                 460

Arg Arg Lys Asn Pro Gln Glu Gly Leu Tyr Asn Glu Leu Gln Lys Asp
465                 470                 475                 480

Lys Met Ala Glu Ala Tyr Ser Glu Ile Gly Met Lys Gly Glu Arg Arg
                485                 490                 495

Arg Gly Lys Gly His Asp Gly Leu Tyr Gln Gly Leu Ser Thr Ala Thr
            500                 505                 510

Lys Asp Thr Tyr Asp Ala Leu His Met Gln Ala Leu Pro Pro Arg
            515                 520                 525
```

<210> SEQ ID NO 31
<211> LENGTH: 501
<212> TYPE: PRT
<213> ORGANISM: Artificial Sequence
<220> FEATURE:
<223> OTHER INFORMATION: anti-GD2 CAR, huKM666-HNG-CD28OXZ
<400> SEQUENCE: 31

```
Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190

Lys Ser Gly Lys Ala Pro Lys Val Trp Ile Tyr Ser Thr Ser Asn Leu
        195                 200                 205

Ala Ser Gly Val Pro Ser Arg Phe Ser Gly Ser Gly Ser Gly Thr Asp
    210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
                245                 250                 255
```

Lys Val Glu Ile Lys Arg Ser Asp Pro Ala Glu Pro Lys Ser Pro Asp
            260                 265                 270

Lys Thr His Thr Cys Pro Pro Cys Pro Lys Asp Pro Lys Phe Trp Val
            275                 280                 285

Leu Val Val Val Gly Gly Val Leu Ala Cys Tyr Ser Leu Leu Val Thr
            290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
            325                 330                 335

Lys His Tyr Gln Pro Tyr Ala Pro Pro Arg Asp Phe Ala Ala Tyr Arg
            340                 345                 350

Ser Arg Asp Gln Arg Leu Pro Pro Asp Ala His Lys Pro Pro Gly Gly
            355                 360                 365

Gly Ser Phe Arg Thr Pro Ile Gln Glu Glu Gln Ala Asp Ala His Ser
            370                 375                 380

Thr Leu Ala Lys Ile Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
            405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
            435                 440                 445

Asn Glu Leu Gln Lys Asp Lys Met Ala Glu Ala Tyr Ser Glu Ile Gly
            450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
            485                 490                 495

Ala Leu Pro Pro Arg
            500

<210> SEQ ID NO 32
<211> LENGTH: 642
<212> TYPE: PRT
<213> ORGANISM: Artificial Sequence
<220> FEATURE:
<223> OTHER INFORMATION: anti-GD2 CAR, huKM666-HCH2CH3pvaa-CD28tmZ

<400> SEQUENCE: 32

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
            35                  40                  45

Leu Ala Ser Tyr Asn Ile His Trp Val Arg Gln Pro Pro Gly Lys Gly
            50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
            85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
            115                 120                 125

Gly Gln Gly Thr Leu Val Thr Val Ser Ser Gly Gly Gly Ser Gly
    130                 135                 140

Gly Gly Gly Ser Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
                180                 185                 190

Lys Ser Gly Lys Ala Pro Lys Val Trp Ile Tyr Ser Thr Ser Asn Leu
    195                 200                 205

Ala Ser Gly Val Pro Ser Arg Phe Ser Gly Ser Gly Ser Gly Thr Asp
    210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
                245                 250                 255

Lys Val Glu Ile Lys Arg Ser Asp Pro Ala Glu Pro Lys Ser Pro Asp
    260                 265                 270

Lys Thr His Thr Cys Pro Pro Cys Pro Ala Pro Pro Val Ala Gly Pro
    275                 280                 285

Ser Val Phe Leu Phe Pro Pro Lys Pro Lys Asp Thr Leu Met Ile Ala
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
                340                 345                 350

Val Ser Val Leu Thr Val Leu His Gln Asp Trp Leu Asn Gly Lys Glu
    355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
                420                 425                 430

Ser Asn Gly Gln Pro Glu Asn Asn Tyr Lys Thr Thr Pro Pro Val Leu
    435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
        500                 505                 510

Ala Cys Tyr Ser Leu Leu Val Thr Val Ala Phe Ile Ile Phe Trp Val
    515                 520                 525

```
Arg Ser Arg Val Lys Phe Ser Arg Ser Ala Asp Ala Pro Ala Tyr Gln
        530                 535                 540

Gln Gly Gln Asn Gln Leu Tyr Asn Glu Leu Asn Leu Gly Arg Arg Glu
545                 550                 555                 560

Glu Tyr Asp Val Leu Asp Lys Arg Arg Gly Arg Asp Pro Glu Met Gly
                565                 570                 575

Gly Lys Pro Arg Arg Lys Asn Pro Gln Glu Gly Leu Tyr Asn Glu Leu
                580                 585                 590

Gln Lys Asp Lys Met Ala Glu Ala Tyr Ser Glu Ile Gly Met Lys Gly
            595                 600                 605

Glu Arg Arg Arg Gly Lys Gly His Asp Gly Leu Tyr Gln Gly Leu Ser
            610                 615                 620

Thr Ala Thr Lys Asp Thr Tyr Asp Ala Leu His Met Gln Ala Leu Pro
625                 630                 635                 640

Pro Arg

<210> SEQ ID NO 33
<211> LENGTH: 681
<212> TYPE: PRT
<213> ORGANISM: Artificial Sequence
<220> FEATURE:
<223> OTHER INFORMATION: anti-GD2 CAR, huMK666-HCH2CH3pvaa-CD28Z

<400> SEQUENCE: 33

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190

Lys Ser Gly Lys Ala Pro Lys Val Trp Ile Tyr Ser Thr Ser Asn Leu
        195                 200                 205

Ala Ser Gly Val Pro Ser Arg Phe Ser Gly Ser Gly Ser Gly Thr Asp
    210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
```

```
            245                 250                 255
Lys Val Glu Ile Lys Arg Ser Asp Pro Ala Glu Pro Lys Ser Pro Asp
            260                 265                 270

Lys Thr His Thr Cys Pro Pro Cys Pro Ala Pro Pro Val Ala Gly Pro
            275                 280                 285

Ser Val Phe Leu Phe Pro Pro Lys Pro Lys Asp Thr Leu Met Ile Ala
            290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                    325                 330                 335

Ala Lys Thr Lys Pro Arg Glu Glu Gln Tyr Asn Ser Thr Tyr Arg Val
                340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
            450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
                500                 505                 510

Ala Cys Tyr Ser Leu Leu Val Thr Val Ala Phe Ile Ile Phe Trp Val
            515                 520                 525

Arg Ser Lys Arg Ser Arg Leu Leu His Ser Asp Tyr Met Asn Met Thr
            530                 535                 540

Pro Arg Arg Pro Gly Pro Thr Arg Lys His Tyr Gln Pro Tyr Ala Pro
545                 550                 555                 560

Pro Arg Asp Phe Ala Ala Tyr Arg Ser Arg Val Lys Phe Ser Arg Ser
                565                 570                 575

Ala Asp Ala Pro Ala Tyr Gln Gln Gly Gln Asn Gln Leu Tyr Asn Glu
                580                 585                 590

Leu Asn Leu Gly Arg Arg Glu Glu Tyr Asp Val Leu Asp Lys Arg Arg
            595                 600                 605

Gly Arg Asp Pro Glu Met Gly Gly Lys Pro Arg Arg Lys Asn Pro Gln
            610                 615                 620

Glu Gly Leu Tyr Asn Glu Leu Gln Lys Asp Lys Met Ala Glu Ala Tyr
625                 630                 635                 640

Ser Glu Ile Gly Met Lys Gly Glu Arg Arg Arg Gly Lys Gly His Asp
                645                 650                 655

Gly Leu Tyr Gln Gly Leu Ser Thr Ala Thr Lys Asp Thr Tyr Asp Ala
            660                 665                 670
```

Leu His Met Gln Ala Leu Pro Pro Arg
        675                 680

<210> SEQ ID NO 34
<211> LENGTH: 1103
<212> TYPE: PRT
<213> ORGANISM: Artificial Sequence
<220> FEATURE:
<223> OTHER INFORMATION: anti-GD2 CAR co-expressed with iCasp9 suicide
      gene

<400> SEQUENCE: 34

Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
    130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
            180                 185                 190

Ala Lys Lys Met Val Leu Ala Leu Leu Glu Leu Ala Gln Gln Asp His
        195                 200                 205

Gly Ala Leu Asp Cys Cys Val Val Val Ile Leu Ser His Gly Cys Gln
    210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
    290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp

```
              340                 345                 350
Asp Ile Phe Glu Gln Trp Ala His Ser Glu Asp Leu Gln Ser Leu Leu
            355                 360                 365
Leu Arg Val Ala Asn Ala Val Ser Val Lys Gly Ile Tyr Lys Gln Met
            370                 375                 380
Pro Gly Cys Phe Asn Phe Leu Arg Lys Lys Leu Phe Phe Lys Thr Ser
385                 390                 395                 400
Ala Ser Arg Ala Glu Gly Arg Gly Ser Leu Leu Thr Cys Gly Asp Val
                    405                 410                 415
Glu Glu Asn Pro Gly Pro Met Glu Thr Asp Thr Leu Leu Leu Trp Val
                420                 425                 430
Leu Leu Leu Trp Val Pro Gly Ser Thr Gly Gln Val Gln Leu Gln Glu
            435                 440                 445
Ser Gly Pro Gly Leu Val Lys Pro Ser Gln Thr Leu Ser Ile Thr Cys
            450                 455                 460
Thr Val Ser Gly Phe Ser Leu Ala Ser Tyr Asn Ile His Trp Val Arg
465                 470                 475                 480
Gln Pro Pro Gly Lys Gly Leu Glu Trp Leu Gly Val Ile Trp Ala Gly
                    485                 490                 495
Gly Ser Thr Asn Tyr Asn Ser Ala Leu Met Ser Arg Leu Thr Ile Ser
                500                 505                 510
Lys Asp Asn Ser Lys Asn Gln Val Phe Leu Lys Met Ser Ser Leu Thr
            515                 520                 525
Ala Ala Asp Thr Ala Val Tyr Tyr Cys Ala Lys Arg Ser Asp Asp Tyr
            530                 535                 540
Ser Trp Phe Ala Tyr Trp Gly Gln Gly Thr Leu Val Thr Val Ser Ser
545                 550                 555                 560
Gly Gly Gly Gly Ser Gly Gly Gly Gly Ser Gly Gly Gly Gly Ser Glu
                    565                 570                 575
Asn Gln Met Thr Gln Ser Pro Ser Ser Leu Ser Ala Ser Val Gly Asp
                580                 585                 590
Arg Val Thr Met Thr Cys Arg Ala Ser Ser Ser Val Ser Ser Ser Tyr
            595                 600                 605
Leu His Trp Tyr Gln Gln Lys Ser Gly Lys Ala Pro Lys Val Trp Ile
            610                 615                 620
Tyr Ser Thr Ser Asn Leu Ala Ser Gly Val Pro Ser Arg Phe Ser Gly
625                 630                 635                 640
Ser Gly Ser Gly Thr Asp Tyr Thr Leu Thr Ile Ser Ser Leu Gln Pro
                    645                 650                 655
Glu Asp Phe Ala Thr Tyr Tyr Cys Gln Gln Tyr Ser Gly Tyr Pro Ile
                660                 665                 670
Thr Phe Gly Gln Gly Thr Lys Val Glu Ile Lys Arg Ser Asp Pro Ala
            675                 680                 685
Glu Pro Lys Ser Pro Asp Lys Thr His Thr Cys Pro Pro Cys Pro Ala
            690                 695                 700
Pro Pro Val Ala Gly Pro Ser Val Phe Leu Phe Pro Pro Lys Pro Lys
705                 710                 715                 720
Asp Thr Leu Met Ile Ala Arg Thr Pro Glu Val Thr Cys Val Val Val
                    725                 730                 735
Asp Val Ser His Glu Asp Pro Glu Val Lys Phe Asn Trp Tyr Val Asp
                740                 745                 750
Gly Val Glu Val His Asn Ala Lys Thr Lys Pro Arg Glu Glu Gln Tyr
            755                 760                 765
```

-continued

```
Asn Ser Thr Tyr Arg Val Val Ser Val Leu Thr Val Leu His Gln Asp
    770                 775                 780

Trp Leu Asn Gly Lys Glu Tyr Lys Cys Lys Val Ser Asn Lys Ala Leu
785                 790                 795                 800

Pro Ala Pro Ile Glu Lys Thr Ile Ser Lys Ala Lys Gly Gln Pro Arg
                805                 810                 815

Glu Pro Gln Val Tyr Thr Leu Pro Pro Ser Arg Asp Glu Leu Thr Lys
            820                 825                 830

Asn Gln Val Ser Leu Thr Cys Leu Val Lys Gly Phe Tyr Pro Ser Asp
        835                 840                 845

Ile Ala Val Glu Trp Glu Ser Asn Gly Gln Pro Glu Asn Asn Tyr Lys
    850                 855                 860

Thr Thr Pro Pro Val Leu Asp Ser Asp Gly Ser Phe Phe Leu Tyr Ser
865                 870                 875                 880

Lys Leu Thr Val Asp Lys Ser Arg Trp Gln Gln Gly Asn Val Phe Ser
                885                 890                 895

Cys Ser Val Met His Glu Ala Leu His Asn His Tyr Thr Gln Lys Ser
            900                 905                 910

Leu Ser Leu Ser Pro Gly Lys Lys Asp Pro Lys Phe Trp Val Leu Val
        915                 920                 925

Val Val Gly Gly Val Leu Ala Cys Tyr Ser Leu Leu Val Thr Val Ala
    930                 935                 940

Phe Ile Ile Phe Trp Val Arg Ser Lys Arg Ser Arg Leu Leu His Ser
945                 950                 955                 960

Asp Tyr Met Asn Met Thr Pro Arg Arg Pro Gly Pro Thr Arg Lys His
                965                 970                 975

Tyr Gln Pro Tyr Ala Pro Pro Arg Asp Phe Ala Ala Tyr Arg Ser Arg
            980                 985                 990

Val Lys Phe Ser Arg Ser Ala Asp  Ala Pro Ala Tyr Gln  Gln Gly Gln
        995                 1000                1005

Asn Gln  Leu Tyr Asn Glu Leu  Asn Leu Gly Arg Arg  Glu Glu Tyr
    1010                1015                1020

Asp Val  Leu Asp Lys Arg Arg  Gly Arg Asp Pro Glu  Met Gly Gly
    1025                1030                1035

Lys Pro  Arg Arg Lys Asn Pro  Gln Glu Gly Leu Tyr  Asn Glu Leu
    1040                1045                1050

Gln Lys  Asp Lys Met Ala Glu  Ala Tyr Ser Glu Ile  Gly Met Lys
    1055                1060                1065

Gly Glu  Arg Arg Arg Gly Lys  Gly His Asp Gly Leu  Tyr Gln Gly
    1070                1075                1080

Leu Ser  Thr Ala Thr Lys Asp  Thr Tyr Asp Ala Leu  His Met Gln
    1085                1090                1095

Ala Leu  Pro Pro Arg
    1100

<210> SEQ ID NO 35
<211> LENGTH: 858
<212> TYPE: PRT
<213> ORGANISM: Artificial Sequence
<220> FEATURE:
<223> OTHER INFORMATION: anti-GD2 CAR co-expressed with RQR8 suicide
      gene

<400> SEQUENCE: 35

Met Gly Thr Ser Leu Leu Cys Trp Met Ala Leu Cys Leu Leu Gly Ala
```

-continued

```
1               5               10              15
Asp His Ala Asp Ala Cys Pro Tyr Ser Asn Pro Ser Leu Cys Ser Gly
             20              25              30

Gly Gly Gly Ser Glu Leu Pro Thr Gln Gly Thr Phe Ser Asn Val Ser
             35              40              45

Thr Asn Val Ser Pro Ala Lys Pro Thr Thr Ala Cys Pro Tyr Ser
 50              55              60

Asn Pro Ser Leu Cys Ser Gly Gly Gly Ser Pro Ala Pro Arg Pro
 65              70              75              80

Pro Thr Pro Ala Pro Thr Ile Ala Ser Gln Pro Leu Ser Leu Arg Pro
             85              90              95

Glu Ala Cys Arg Pro Ala Ala Gly Gly Ala Val His Thr Arg Gly Leu
             100             105             110

Asp Phe Ala Cys Asp Ile Tyr Ile Trp Ala Pro Leu Ala Gly Thr Cys
             115             120             125

Gly Val Leu Leu Leu Ser Leu Val Ile Thr Leu Tyr Cys Asn His Arg
             130             135             140

Asn Arg Arg Arg Val Cys Lys Cys Pro Arg Pro Val Val Arg Ala Glu
145             150             155             160

Gly Arg Gly Ser Leu Leu Thr Cys Gly Asp Val Glu Glu Asn Pro Gly
             165             170             175

Pro Met Glu Thr Asp Thr Leu Leu Leu Trp Val Leu Leu Leu Trp Val
             180             185             190

Pro Gly Ser Thr Gly Gln Val Gln Leu Gln Glu Ser Gly Pro Gly Leu
             195             200             205

Val Lys Pro Ser Gln Thr Leu Ser Ile Thr Cys Thr Val Ser Gly Phe
 210             215             220

Ser Leu Ala Ser Tyr Asn Ile His Trp Val Arg Gln Pro Pro Gly Lys
225             230             235             240

Gly Leu Glu Trp Leu Gly Val Ile Trp Ala Gly Gly Ser Thr Asn Tyr
             245             250             255

Asn Ser Ala Leu Met Ser Arg Leu Thr Ile Ser Lys Asp Asn Ser Lys
             260             265             270

Asn Gln Val Phe Leu Lys Met Ser Ser Leu Thr Ala Ala Asp Thr Ala
             275             280             285

Val Tyr Tyr Cys Ala Lys Arg Ser Asp Tyr Ser Trp Phe Ala Tyr
             290             295             300

Trp Gly Gln Gly Thr Leu Val Thr Val Ser Gly Gly Gly Gly Ser
305             310             315             320

Gly Gly Gly Gly Ser Gly Gly Gly Ser Glu Asn Gln Met Thr Gln
             325             330             335

Ser Pro Ser Ser Leu Ser Ala Ser Val Gly Asp Arg Val Thr Met Thr
             340             345             350

Cys Arg Ala Ser Ser Ser Val Ser Ser Ser Tyr Leu His Trp Tyr Gln
             355             360             365

Gln Lys Ser Gly Lys Ala Pro Lys Val Trp Ile Tyr Ser Thr Ser Asn
             370             375             380

Leu Ala Ser Gly Val Pro Ser Arg Phe Ser Gly Ser Gly Ser Gly Thr
385             390             395             400

Asp Tyr Thr Leu Thr Ile Ser Ser Leu Gln Pro Glu Asp Phe Ala Thr
             405             410             415

Tyr Tyr Cys Gln Gln Tyr Ser Gly Tyr Pro Ile Thr Phe Gly Gln Gly
             420             425             430
```

```
Thr Lys Val Glu Ile Lys Arg Ser Asp Pro Ala Glu Pro Lys Ser Pro
            435                 440                 445

Asp Lys Thr His Thr Cys Pro Pro Cys Pro Ala Pro Pro Val Ala Gly
    450                 455                 460

Pro Ser Val Phe Leu Phe Pro Pro Lys Pro Lys Asp Thr Leu Met Ile
465                 470                 475                 480

Ala Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
                500                 505                 510

Asn Ala Lys Thr Lys Pro Arg Glu Glu Gln Tyr Asn Ser Thr Tyr Arg
            515                 520                 525

Val Val Ser Val Leu Thr Val Leu His Gln Asp Trp Leu Asn Gly Lys
            530                 535                 540

Glu Tyr Lys Cys Lys Val Ser Asn Lys Ala Leu Pro Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Ser Arg Asp Glu Leu Thr Lys Asn Gln Val Ser Leu
            580                 585                 590

Thr Cys Leu Val Lys Gly Phe Tyr Pro Ser Asp Ile Ala Val Glu Trp
            595                 600                 605

Glu Ser Asn Gly Gln Pro Glu Asn Asn Tyr Lys Thr Thr Pro Pro Val
            610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys Lys Asp Pro Lys Phe Trp Val Leu Val Val Val Gly Gly Val
            675                 680                 685

Leu Ala Cys Tyr Ser Leu Leu Val Thr Val Ala Phe Ile Ile Phe Trp
    690                 695                 700

Val Arg Ser Lys Arg Ser Arg Leu Leu His Ser Asp Tyr Met Asn Met
705                 710                 715                 720

Thr Pro Arg Arg Pro Gly Pro Thr Arg Lys His Tyr Gln Pro Tyr Ala
                725                 730                 735

Pro Pro Arg Asp Phe Ala Ala Tyr Arg Ser Arg Val Lys Phe Ser Arg
                740                 745                 750

Ser Ala Asp Ala Pro Ala Tyr Gln Gln Gly Gln Asn Gln Leu Tyr Asn
            755                 760                 765

Glu Leu Asn Leu Gly Arg Arg Glu Glu Tyr Asp Val Leu Asp Lys Arg
    770                 775                 780

Arg Gly Arg Asp Pro Glu Met Gly Gly Lys Pro Arg Arg Lys Asn Pro
785                 790                 795                 800

Gln Glu Gly Leu Tyr Asn Glu Leu Gln Lys Asp Lys Met Ala Glu Ala
                805                 810                 815

Tyr Ser Glu Ile Gly Met Lys Gly Glu Arg Arg Arg Gly Lys Gly His
                820                 825                 830

Asp Gly Leu Tyr Gln Gly Leu Ser Thr Ala Thr Lys Asp Thr Tyr Asp
            835                 840                 845
```

```
Ala Leu His Met Gln Ala Leu Pro Pro Arg
    850                 855
```

<210> SEQ ID NO 36
<211> LENGTH: 402
<212> TYPE: PRT
<213> ORGANISM: Artificial Sequence
<220> FEATURE:
<223> OTHER INFORMATION: Inducible Caspase 9 (iCasp9) sequence

<400> SEQUENCE: 36

```
Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
    130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
            180                 185                 190

Ala Lys Lys Met Val Leu Ala Leu Leu Glu Leu Ala Gln Gln Asp His
        195                 200                 205

Gly Ala Leu Asp Cys Cys Val Val Val Ile Leu Ser His Gly Cys Gln
    210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
    290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
            340                 345                 350
```

```
Asp Ile Phe Glu Gln Trp Ala His Ser Glu Asp Leu Gln Ser Leu Leu
            355                 360                 365

Leu Arg Val Ala Asn Ala Val Ser Val Lys Gly Ile Tyr Lys Gln Met
        370                 375                 380

Pro Gly Cys Phe Asn Phe Leu Arg Lys Lys Leu Phe Phe Lys Thr Ser
385                 390                 395                 400

Ala Ser

<210> SEQ ID NO 37
<211> LENGTH: 157
<212> TYPE: PRT
<213> ORGANISM: Artificial Sequence
<220> FEATURE:
<223> OTHER INFORMATION: Novel marker/suicide gene RQR8 sequence

<400> SEQUENCE: 37

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val
145                 150                 155
```

CHIMERIC ANTIGEN RECEPTOR

CROSS-REFERENCE TO RELATED APPLICATIONS

This is a Continuation of U.S. application Ser. No. 15/123,331 filed Sep. 2, 2016, which is a U.S. National Phase of International Application No. PCT/GB2015/50649, filed Mar. 6, 2015, which claims priority to Great Britain Application No. 1403972.1, filed Mar. 6, 2014.

FIELD OF THE INVENTION

The present invention relates to chimeric antigen receptor (CAR) which binds the cancer antigen disialoganglioside (GD2). T cells expressing such a CAR are useful in the treatment of cancerous diseases such as neuroblastoma.

BACKGROUND TO THE INVENTION

Disialoganglioside (GD2, pubchem: 6450346) is a sialic acid-containing glycosphingolipid expressed primarily on the cell surface. The function of this carbohydrate antigen is not completely understood; however, it is thought to play an important role in the attachment of tumour cells to extracellular matrix proteins. GD2 is densely, homogenously and almost universally expressed on neuroblastoma. In normal tissues, GD2 expression is largely limited to skin melanocytes, and peripheral pain fibre myelin sheaths. Within the CNS, GD2 appears to be an embryonic antigen but is found dimly expressed in scattered oligodendrocytes and within the posterior pituitary. This makes GD2 well suited for targeted antitumour therapy.

Anti-GD2 antibodies have been extensively tested as therapy in neuroblastoma. Two clones and their derivatives are in current clinical use: clone 3F814 and 3F8. Another clone 14.187 has been tested as a mouse IgG3, after isotype switching to IgG2a (14g2a) and finally after chimerization with human IgG1 to form ch14.18. This latter antibody has resulted in clear efficacy in a randomized study: the US Children's Oncology Group reported a randomised phase III study of ch14:18 in children with high-risk neuroblastoma who had achieved radiological remission after initial treatment. In these patients, there was a 20% improvement in EFS in the ch14:18 arm with a mean follow-up of 2.1 years. Importantly, neurotoxicity most commonly as a chronic pain inducing neuropathy and less commonly an ophthalmoplegia is the main dose-limiting toxicity with these agents.

These therapeutic mAbs continue to be refined: an IL-2 immunocytokine derived from ch14.18 has been described. This is quite a toxic agent with some effect on minimal residual disease, but none against bulky disease. Ch14.18 has been fully humanized and its Fc mutated to inhibit complement activation. This humanized version of Ch14.18 is in clinical study but only very limited data are available. Humanization of the 3F8 antibody has also been described. While clinical data from GD2 serotherapy is encouraging, sustained complete remissions are still limited and there is no evidence for a clinically useful role for antibodies except in the minimal disease setting.

There is thus a need for improved therapeutic approaches to treat neuroblastoma and other GD2-expressing cancers.

Chimeric Antigen Receptors (CARs)

Chimeric antigen receptors are proteins which, in their usual format, graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1a).

The most common form of these molecules are fusions of single-chain variable fragments (scFv) derived from monoclonal antibodies which recognise a target antigen, fused via a spacer and a transmembrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

Chimeric antigen receptors against GD2 have been described in which the antigen-binding domain is based on the scFv 14g2a (WO 2013/040371 and Yvon et al (2009, Clin Cancer Res 15:5852-5860)).

Human T cells expressing a 14g2a-CD28-OX40-ξ CAR was shown to have some anti-tumour activity but to be unable to completely eradicate the disease (Yvon et al (2009) as above).

The present inventors sought to make an alternative GD2-targeting CAR with improved properties.

DESCRIPTION OF THE FIGURES

FIG. 4. (a) Retroviral construct allowing 1:1 co-expression of CD34 marker gene with CAR; (b) Flow cytometric analysis of CAR expression (HA tag) vs CD34 marker gene; (c) Chromium release assay of non-transduced T-cells and T-cells transduced with the 3 different CAR variants against GD2 positive targets (LAN-1), and GD2 negative targets (A204); (d) Interferon gamma release; (e) IL-2 release; and (f) proliferation of the same targets and effectors.

FIG. 6—Optimization of the Expression Cassette (a) map optimizations which were introduced into the cassette: SAR or CHS4; (b) representative expression of CAR with different modifications with either wt or codon-optimized open-reading frame. The SAR construct gives a tight peak of expression which is what is desired. (c) Bar chart representation of this FACS data from 3 normal donors.

Three different chimeric antigen receptors were compared. The receptors all comprised of the huK666 scFv, the Fc domain of IgG1 mutated to reduce FcR binding and the CD28 transmembrane domain. CAR "28tmZ" has a CD3 Zeta endodomain; "28Z" has a compound CD28-CD3Zeta endodomain; "28OXZ" has a compound endodomain comprising of CD28, OX40 and CD3Zeta, Peripheral blood T-cells from normal donors were transduced with these constructs with retroviral vectors of similar titers. These different T-cell lines were compared, along with non-transduced T-cells as controls. T-cells were challenged with A204 cells (a rhabdomyosarcoma cell line which is GD2 negative), and LAN-1 cells (a neuroblastoma cell line which is GD2 positive). Proliferation and cytokine release show that receptor activity is 28tmZ<28Z<28OXZ.

Figure 8:
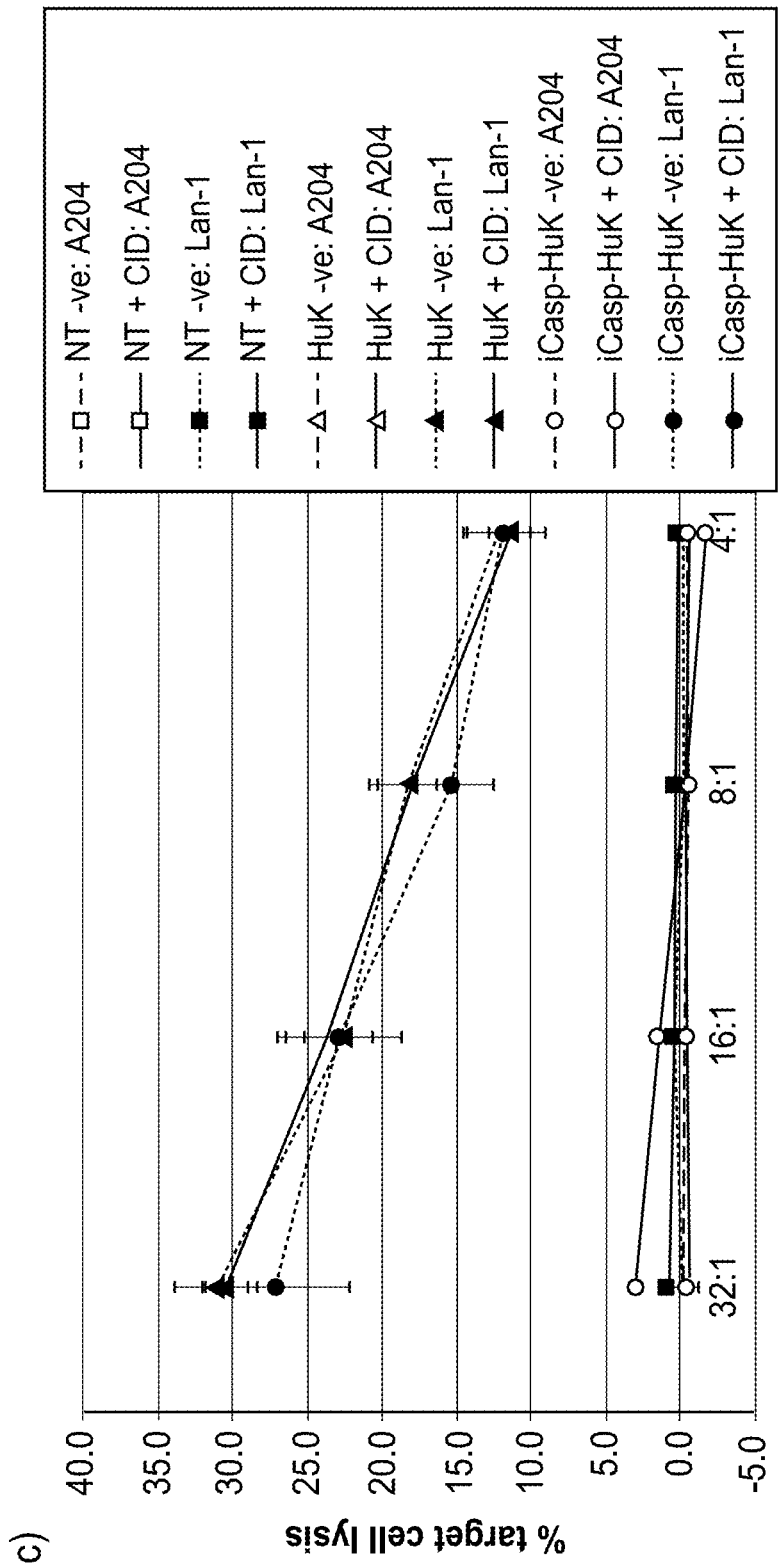

FIG. 8—Co-expression with iCasp9 suicide gene (a) Co-expression of iCasp9 with anti-GD2CAR using FMD-2A sequence; (b) CAR expression in NT T-cells, GD2CAR transduced T-cells and iCasp9-2A-GD2CAR T-cells alone and after treatment with CID; (c) Killing of GD2 positive (LAN-1) and negative (A204) targets with non-transduced, GD2CAR transduced and iCasp9-2A-GD2CAR transduced T-cells with or without treatment with CID. Average of 5 normal donor T-cells.

FIG. 9—Co-expression with RQR8 suicide gene (a) CARhuK666Fc was co-expressed with the RQR8 sort-suicide gene in a retroviral vector. (b) T-cells were transduced with this retroviral vector and co-expression of the CAR and RQR8 was determined by staining the transduced T-cells with a polyclonal anti-Fc and the monoclonal antibody QBend10. (c) The CAR positive population from these T-cells could be depleted in the presence of Rituximab and complement. (d) T-cells depleted with Rituximab no longer recognized GD2 expressing targets.

Figure 10:
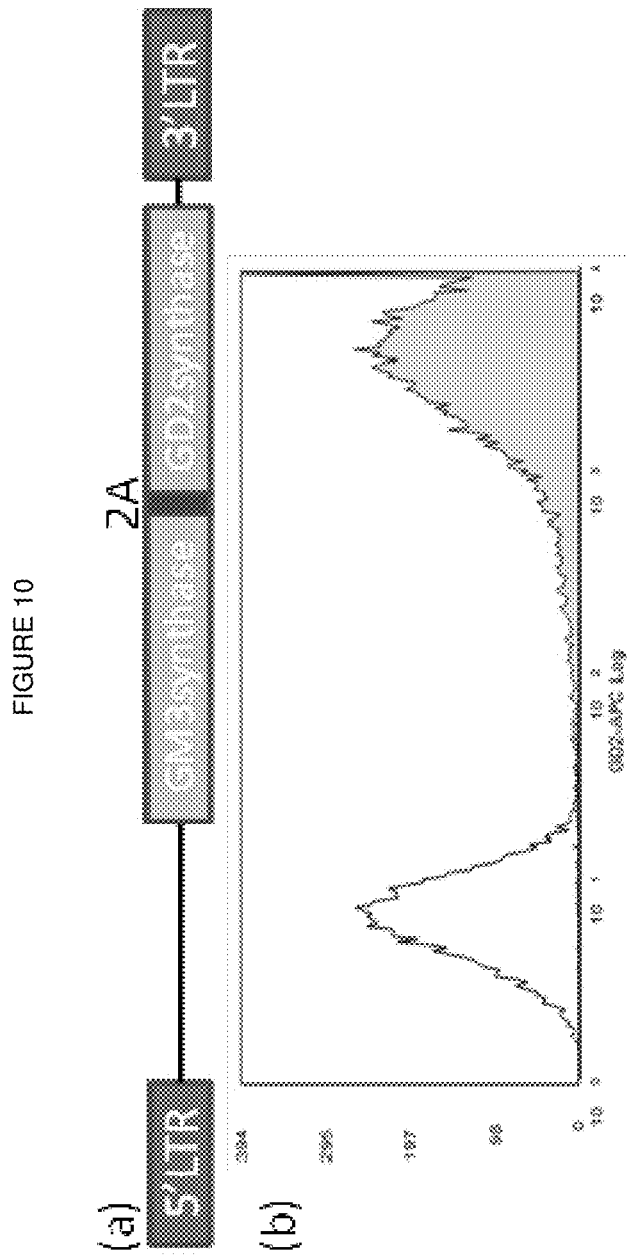

FIG. 10—(a) Bicistronic vector expressing GM3synthase and GD2synthase. (b) SupT1 cells transduced with this vector become GD2 positive (non-transduced empty plot; transduced greyed plot).

Figure 11:
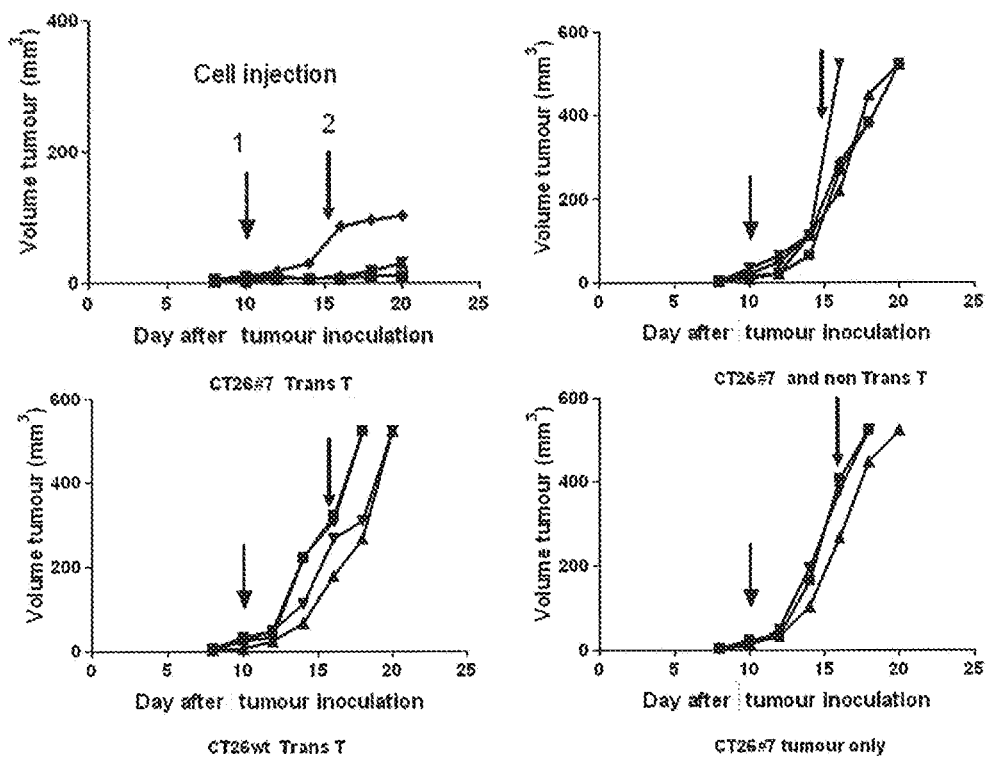

FIG. 11—Growth curves of individual tumours in mice in the following cohorts: top left: mice with GD2 expressing CT26 tumours receiving anti-GD2 CAR splenocytes; top right: GD2 expressing CT26 tumours receiving mock-transduced splenocytes; bottom left: GD2 negative (wt) CT26 tumours with anti-GD2 CAR splenocytes; bottom right: and GD2 expressing CT26 tumours receiving no splenocytes FIG. 12—Amino Acid Sequences A. anti-GD2 CAR shown as (a) in FIG. 2 (muKM666-HCH2CH3-CD28OXZ—SEQ ID No. 26)

Figure 1:
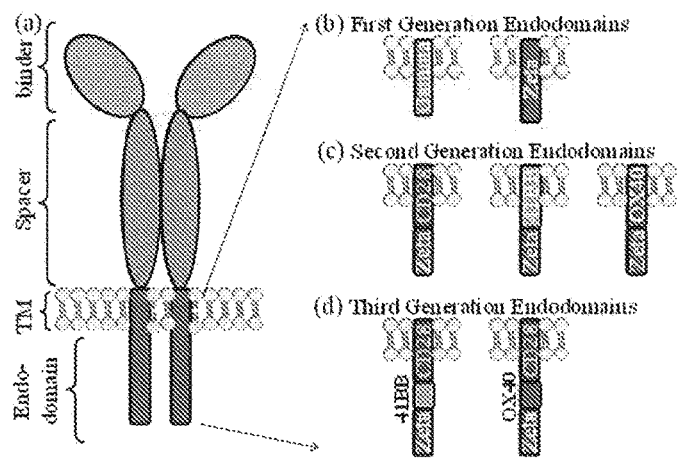
FIG. 1—Chimeric Antigen Receptor (CAR) design.
(a) generalized architecture of a CAR: A binding domain recognizes antigen; the spacer elevates the binding domain from the cell surface; the trans-membrane domain anchors the protein to the membrane and the endodomain transmits signals. (b) to (d): Different generations and permutations of CAR endodomains: (b) initial designs transmitted ITAM signals alone through FcεR1-γ or CD3☐ endodomain, while later designs transmitted additional (c) one or (d) two co-stimulatory signals in cis.
Figure 2:
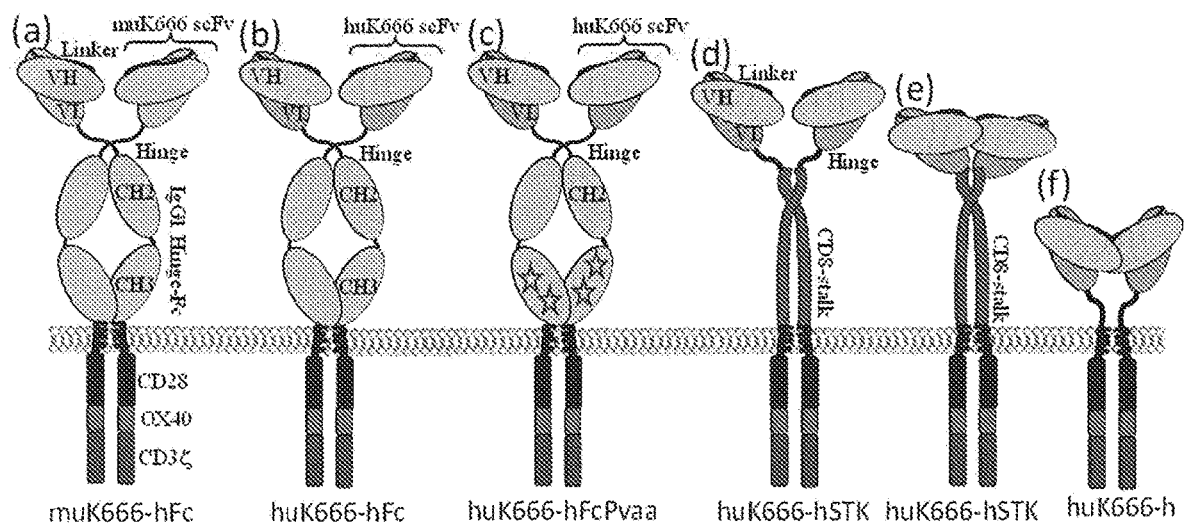
FIG. 2—Variants of anti-GD2 CARs constructed (a) anti-GD2 CAR using mouse KM666 antibody as scFv with human IgG1 spacer and CD28-OX40-Zeta endodomain; (b) anti-GD2 CAR using Nakamura humanized antibody huKM666 in the same format as (a); (c) same format as (b) except Fc domain is modified to remove Fc Receptor recognition motifs; (d) same format as (c) except spacer is IgG1 hinge—CD8 stalk; (e) same as (c) except spacer is CD8 stalk only; (f) same as (c) except spacer is IgG1 hinge only.

B. anti-GD2 CAR shown as (b) in FIG. 2 (huKM666-HCH2CH3-CD28OXZ—SEQ ID No. 27)

C. anti-GD2 CAR shown as (c) in FIG. 2 (huKM666-HCH2CH3pvaa-CD28OXZ—SEQ ID No. 28)

D. anti-GD2 CAR shown as (d) in FIG. 2 (huKM666-HSTK-CD28OXZ—SEQ ID No. 29)

E. anti-GD2 CAR shown as (e) in FIG. 2 (huKM666-STK-CD28XOXZ—SEQ ID No. 30)

F. anti-GD2 CAR shown as (f) in FIG. 2 (huKM666-HNG-CD28OXZ—SEQ ID No. 31)

G. anti-GD2 CAR as shown in (c) FIG. 2 but with 1st generation endodomain (huKM666-HCH2CH3pvaa-CD28tmZ—SEQ ID No. 32)

H. anti-GD2 CAR as shown in (c) FIG. 2 but with 2nd generation endodomain (huMK666-HCH2CH3pvaa-CD28Z—SEQ ID No. 33)

I. anti-GD2 CAR co-expressed with iCasp9 suicide gene—SEQ ID No. 34

J. anti-GD2 CAR co-expressed with RQR8 suicide gene—SEQ ID No. 35

Figure 13:
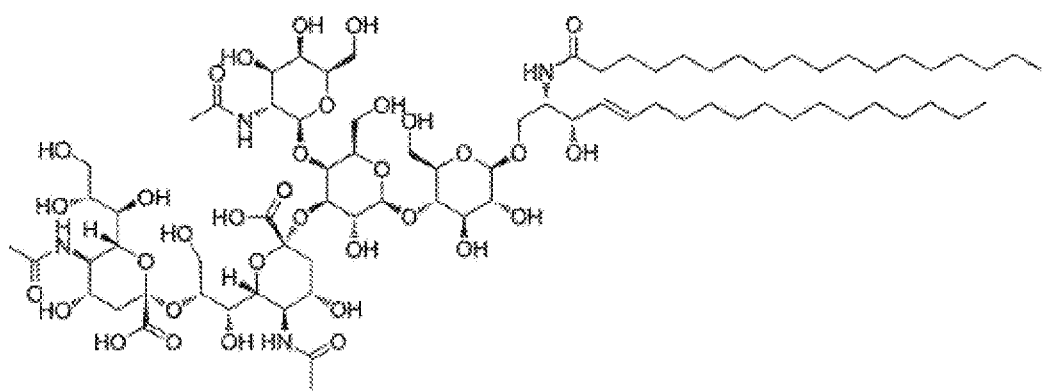

FIG. 13—Structure of GD2

Figure 14:
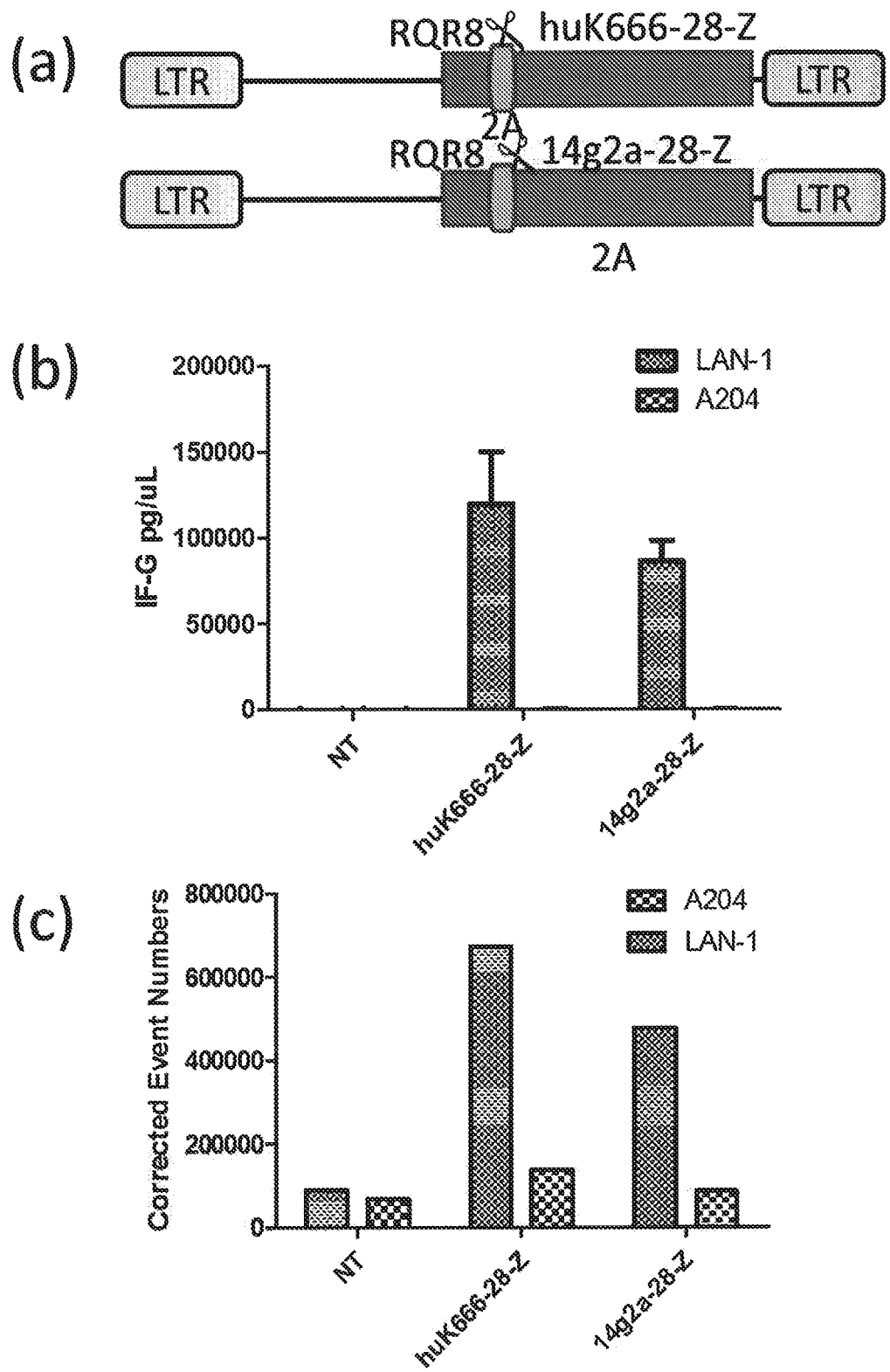

FIG. 14—Comparison of huK666 and 14g2a CARs. (a) maps of constructs tested: Two constructs were tested in primary T-cells. Both are retroviral vectors coding for RQR8 and a 2nd generation GD2 CAR co-expressed with a FMD-2A like sequence. The only difference between constructs is that in one, the scFv is huK666 and in the other it is 14g2a. T-cells transduced with these constructs were challenged 1:1 with either A204 (a GD2 negative rhabdomyosarcoma cell line), and LAN-1 (a GD2 positive cell line). (b) At 24 hours, Interferon-gamma was measured from supernatant. huK666 CAR T-cells produce more IF-G. (c) After one week T-cells are counted, huK666 show more proliferation.

Figure 15:
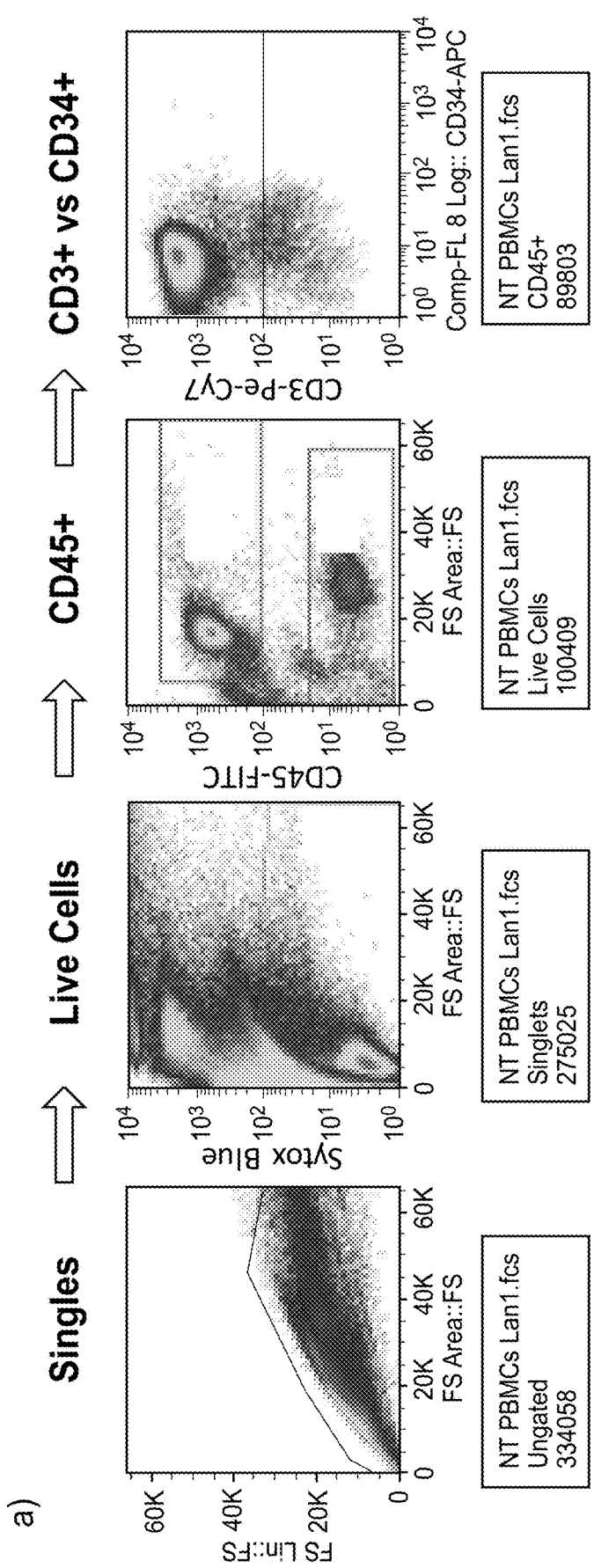

FIG. 15—Flow cytometric analysis of co-culture between huK666 or 14g2a based 2nd generation CARs and Neuroblastoma cell line LAN1. (a) Set up of the experiment. After one week co-culture, cells were harvested and analyzed by flow-cytometry. CD45 expression allowed discrimination from lymphoid cells and non-lymphoid cells with CD45− cells being LAN-1 cells. Further staining with CD3/QBEND/10 allowed counting of CAR T-cells. (b) T-cells alone; (c) NT T-cells and LAN-1 cells; (d) huK666-28-Z CAR T-cells and LAN-1 cells; (e) 14g2a-28-Z CAR T-cells and LAN-1 cells. A residuum of LAN-1 cells is seen in the 14g2a CAR T-cell co-culture.

SUMMARY OF ASPECTS OF THE INVENTION

The present inventors have constructed a new chimeric antigen receptor (CAR) targeting GD2 which comprises a GD2-binding domain based on the K666 antibody.

The anti-GD2 antibody 14g2a can be seen as the gold standard because it is used as a therapeutic antibody and is the only scFv tested to date in a CAR study (PMID: 18978797). The present inventors compared 14g2a and huK666 based CAR in a second generation format as this is the most widely used CAR format used in clinical studies. We found that huK666 CAR T-cells release more IFN-γ, proliferate better and kill more completely than 14g2a equivalents.

Thus, in a first aspect the present invention provides a chimeric antigen receptor (CAR) comprising a disialoganglioside (GD2)-binding domain which comprises a) a heavy chain variable region (VH) having complementarity determining regions (CDRs) with the following sequences:

```
CDR1
                                       (SEQ ID No. 1)
SYNIH;

CDR2
                                       (SEQ ID No. 2)
VIWAGGSTNYNSALMS

CDR3
                                       (SEQ ID No. 3)
RSDDYSWFAY;
``` and b) a light chain variable region (VL) having CDRs with the following sequences:

```
CDR1
                                       (SEQ ID No. 4)
RASSSVSSSYLH;

CDR2
                                       (SEQ ID No. 5)
STSNLAS

CDR3
                                       (SEQ ID No. 6)
QQYSGYPIT.
```

The GD2 binding domain may comprise a VH domain having the sequence shown as SEQ ID No. 9, or SEQ ID NO 10; or a VL domain having the sequence shown as SEQ ID No 11, or SEQ ID No. 12 or a variant thereof having at least 90% sequence identity which retains the capacity to i) bind GD2 and ii) induce T cell signalling.

The GD2 binding domain may comprise the sequence shown as SEQ ID No 7 or SEQ ID No. 8 or a variant thereof having at least 90% sequence identity which retains the capacity to i) bind GD2 and ii) induce T cell signalling.

The transmembrane domain may comprise the sequence shown as SEQ ID No. 13 or a variant thereof having at least 90% sequence identity which retains the capacity to i) bind GD2 and ii) induce T cell signalling.

The GD2-binding domain and the transmembrane domain may be connected by a spacer.

The spacer may comprise one of the following: a human an IgG1 Fc domain; an IgG1 hinge; an IgG1 hinge-CD8 stalk; or a CD8 stalk.

The spacer may comprise an IgG1 hinge-CD8 stalk or a CD8 stalk.

The spacer may comprise an IgG1 Fc domain or a variant thereof.

The spacer may comprise an IgG1 Fc domain which comprises the sequence shown as SEQ ID No. 23 or SEQ ID No. 24 or a variant thereof having at least 80% sequence identity.

The CAR may comprise or associate with an intracellular T cell signalling domain.

The intracellular T cell signalling domain may comprise one or more of the following endodomains: CD28 endodomain; OX40 and CD3-Zeta endodomain.

The intracellular T cell signalling domain may comprise all of the following endodomains: CD28 endodomain; OX40 and CD3-Zeta endodomain.

The CAR may comprise the sequence shown as any of SEQ ID No. 26 to 35 or a variant thereof which has at least 80% sequence identity but retains the capacity to i) bind GD2 and ii) induce T cell signalling.

In a second aspect, the present invention provides a nucleic acid sequence which encodes a CAR according to the first aspect of the invention.

The nucleic acid sequence may be codon-optimised.

The nucleic acid sequence may comprise the sequence shown as SEQ ID No 25 or a variant thereof having at least 90% sequence identity.

The nucleic acid may also encode a suicide gene.

In a third aspect, the present invention provides a vector which comprises a nucleic acid sequence according to the second aspect of the invention.

In a fourth aspect, the present invention provides a cell which expresses a CAR according to the first aspect of the invention. The cell may be a cytolytic immune cell, such as a T cell or natural killer (NK) cell.

The cell may co-expresses a CAR according to the first aspect of the invention and a suicide gene.

The suicide gene may, for example, be iCasp9 or RQR8.

In a fifth aspect, the present invention provides a method for making a cell according to the fourth aspect of the invention, which comprises the step of introducing a nucleic acid according to the second aspect of the invention into a cell.

In a sixth aspect, the present invention provides a pharmaceutical composition which comprises a vector according to the third aspect of the invention or a cell according to the second aspect of the invention, together with a pharmaceutically acceptable carrier, diluent or excipient.

In a seventh aspect, the present invention provides a method for treating cancer which comprises the step of administering a vector according to the third aspect of the invention or a cell according to the fourth aspect of the invention to a subject.

The cancer may be neuroblastoma.

In an eighth aspect, the present invention provides a vector according to the third aspect of the invention or a cell according to the fourth aspect of the invention for use in treating a cancer.

In a ninth aspect, the present invention provides the use of according to the third aspect of the invention or a cell according to the fourth aspect of the invention in the manufacture of a medicament for treating cancer.

In a tenth aspect, the present invention provides a method for making a GD2-expressing cell which comprises the step of introducing a nucleic acid encoding GM3 synthase and a nucleic acid encoding GD2 synthase into a cell.

In an eleventh aspect, the present invention provides a GD2-expressing cell which comprises a heterologous nucleic acid encoding GM3 synthase and a heterologous nucleic acid encoding GD2 synthase.

In an twelfth aspect, the present invention provides method for stimulating a cell according to the fourth aspect of the invention in vitro, which comprises the step of bringing the cell into contact with a GD2-expressing cell according to the eleventh aspect of the invention.

In a thirteenth aspect, the present invention provides an expression cassette expressing a CAR which comprises a scaffold attachment region (SAR).

The expression cassette may express a CAR according to the first aspect of the invention.

DETAILED DESCRIPTION

Chimeric Antigen Receptors (Cars)

Chimeric antigen receptors (CARs), also known as chimeric T cell receptors, artificial T cell receptors and chimeric immunoreceptors, are engineered receptors, which graft an arbitrary specificity onto an immune effector cell. In a classical CAR, the specificity of a monoclonal antibody is grafted on to a T cell. CAR-encoding nucleic acids may be transferred to T cells using, for example, retroviral vectors. In this way, a large number of cancer-specific T cells can be generated for adoptive cell transfer. Phase I clinical studies of this approach show efficacy.

The target-antigen binding domain of a CAR is commonly fused via a spacer and transmembrane domain to a signaling endodomain. When the CAR binds the target-antigen, this results in the transmission of an activating signal to the T-cell it is expressed on.

The CAR of the present invention comprises a GD2 binding domain which is based on the KM666 monoclonal antibody (Nakamura et al (2001) Cancer Immunol. Immunother. 50:275-284).

The CAR of the present invention comprises a GD2-binding domain which comprises a) a heavy chain variable region (VH) having complementarity determining regions (CDRs) with the following sequences:

```
CDR1
                                  (SEQ ID No. 1)
SYNIH;
CDR2
                                  (SEQ ID No. 2)
VIWAGGSTNYNSALMS
CDR3
                                  (SEQ ID No. 3)
RSDDYSWFAY;
``` and b) a light chain variable region (VL) having CDRs with the following sequences:

```
CDR1
                                  (SEQ ID No. 4)
RASSSVSSSYLH;
CDR2
                                  (SEQ ID No. 5)
STSNLAS
CDR3
                                  (SEQ ID No. 6)
QQYSGYPIT.
```

It may be possible to introduce one or more mutations (substitutions, additions or deletions) into the or each CDR without negatively affecting GD2-binding activity. Each CDR may, for example, have one, two or three amino acid mutations.

The CAR of the present invention may comprise one of the following amino acid sequences:

```
(Murine KM666 sequence)
                                  SEQ ID No. 7
QVQLKESGPVLVAPSQTLSITCTVSGFSLASYNIHWVRQPPGKGLEWLGV

IWAGGSTNYNSALMSRLSISKDNSKSQVFLQMNSLQTDDTAMYYCAKRSD

DYSWFAYWGQGTLVTVSASGGGGSGGGGSGGGGSENVLTQSPAIMSASPG

EKVTMTCRASSSVSSSYLHWYQQKSGASPKVWIYSTSNLASGVPGRFSGS

GSGTSYSLTISSVEAEDAATYYCQQYSGYPITFGAGTKVEVKR
```

```
(Humanised KM666 sequence)
                                  SEQ ID No. 8
QVQLQESGPGLVKPSQTLSITCTVSGFSLASYNIHWVRQPPGKGLEWLGV

IWAGGSTNYNSALMSRLTISKDNSKNQVFLKMSSLTAADTAVYYCAKRSD

DYSWFAYWGQGTLVTVSSGGGGSGGGGSGGGGSENQMTQSPSSLSASVGD

RVTMTCRASSSVSSSYLHWYQQKSGKAPKVWIYSTSNLASGVPSRFSGSG

SGTDYTLTISSLQPEDFATYYCQQYSGYPITFGQGTKVEIKR
```

The CAR of the present invention may comprise one of the following VH sequences:

```
(Murine KM666 VH sequence)
                                  SEQ ID No. 9
QVQLKESGPVLVAPSQTLSITCTVSGFSLASYNIHWVRQPPGKGLEWLGV

IWAGGSTNYNSALMSRLSISKDNSKSQVFLQMNSLQTDDTAMYYCAKRSD

DYSWFAYWGQGTLVTVSA (Humanised KM666 VH sequence)
                                  SEQ ID No. 10
QVQLQESGPGLVKPSQTLSITCTVSGFSLASYNIHWVRQPPGKGLEWLGV

IWAGGSTNYNSALMSRLTISKDNSKNQVFLKMSSLTAADTAVYYCAKRSD

DYSWFAYWGQGTLVTVSS
```

The CAR of the present invention may comprise one of the following VL sequences:

```
(Murine KM666 VL sequence)
                                  SEQ ID No. 11
ENVLTQSPAIMSASPGEKVTMTCRASSSVSSSYLHWYQQKSGASPKVWIY

STSNLASGVPGRFSGSGSGTSYSLTISSVEAEDAATYYCQQYSGYPITFG

AGTKVEVK (Humanised KM666 VH sequence)
                                  SEQ ID No. 12
ENQMTQSPSSLSASVGDRVTMTCRASSSVSSSYLHWYQQKSGKAPKVWIY

STSNLASGVPSRFSGSGSGTDYTLTISSLQPEDFATYYCQQYSGYPITFG

QGTKVEIK
```

The CAR of the invention may comprise a variant of the sequence shown as SEQ ID No. 7, 8, 9, 10, 11 or 12 having at least 80, 85, 90, 95, 98 or 99% sequence identity, provided that the variant sequence retain the capacity to bind GD2 (when in conjunction with a complementary VL or VH domain, if appropriate).

The percentage identity between two polypeptide sequences may be readily determined by programs such as BLAST which is freely available at http://blast.ncbi.nlm.nih.gov.

Transmembrane Domain

The CAR of the invention may also comprise a transmembrane domain which spans the membrane. It may comprise a hydrophobic alpha helix. The transmembrane domain may be derived from CD28, which gives good receptor stability.

The transmembrane domain may comprise the sequence shown as SEQ ID No. 13.

```
                                           SEQ ID No. 13
FWVLVVVGGVLACYSLLVTVAFIIFWV
```

Intracellular T Cell Signaling Domain (Endodomain)

The endodomain is the signal-transmission portion of the CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain of the CAR of the present invention may comprise the CD28 endodomain and OX40 and CD3-Zeta endodomain.

The transmembrane and intracellular T-cell signalling domain (endodomain) of the CAR of the present invention may comprise the sequence shown as SEQ ID No. 14, 15, 16, 17 or 18 or a variant thereof having at least 80% sequence identity.

```
(CD28 endodomain)
                                           SEQ ID No. 14
RSKRSRLLHSDYMNMTPRRPGPTRKHYQPYAPPRDFAAY (CD40 endodomain)
                                           SEQ ID No. 15
RSRDQRLPPDAHKPPGGGSFRTPIQEEQADAHSTLAKI (CD3 zeta endodomain)
                                           SEQ ID No. 16
RSRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATK

DTYDALHMQALPPR (CD28Z)
                                           SEQ ID No. 17
RSKRSRLLHSDYMNMTPRRPGPTRKHYQPYAPPRDFAAYRSRVKFSRSAD

APAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQAL

PPR (CD28OXZ)
                                           SEQ ID No. 18
RSKRSRLLHSDYMNMTPRRPGPTRKHYQPYAPPRDFAAYRSRDQRLPPDA

HKPPGGGSFRTPIQEEQADAHSTLAKIRVKFSRSADAPAYQQGQNQLYNE

LNLGRREEYDVLDKRRGRDPEMGGKPRRKNPQEGLYNELQKDKMAEAYSE

IGMKGERRRGKGHDGLYQGLSTATKDTYDALHMQALPPR
```

A variant sequence may have at least 80%, 85%, 90%, 95%, 98% or 99% sequence identity to SEQ ID No. 13, 14, 15, 16, 17 or 18, provided that the sequence provides an effective transmembrane domain/intracellular T cell signaling domain.

Signal Peptide

The CAR of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The CAR of the invention may have the general formula:

Signal peptide—GD2-binding domain—spacer domain—transmembrane domain—intracellular T cell signaling domain.

The signal peptide may comprise the SEQ ID No. 19 or a variant thereof having 5, 4, 3, 2 or 1 amino acid mutations (insertions, substitutions or additions) provided that the signal peptide still functions to cause cell surface expression of the CAR.

```
         SEQ ID No. 19: METDTLLLWVLLLWVPGSTG
```

The signal peptide of SEQ ID No. 19 is compact and highly efficient. It is predicted to give about 95% cleavage after the terminal glycine, giving efficient removal by signal peptidase.

Spacer

The CAR of the present invention may comprise a spacer sequence to connect the GD2-binding domain with the transmembrane domain and spatially separate the GD2-binding domain from the endodomain. A flexible spacer allows to the GD2-binding domain to orient in different directions to enable GD2 binding.

The spacer sequence may, for example, comprise an IgG1 Fc region, an IgG1 hinge or a CD8 stalk, or a combination thereof. The spacer may alternatively comprise an alternative sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below:

```
(hinge-CH2CH3 of human IgG1)
                                           SEQ ID No. 20
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD
```

(human CD8 stalk):
SEQ ID No. 21
TTTPAPRPPTPAPTIASQPLSLRPEACRPAAGGAVHTRGLDFACDl (human IgG1 hinge):
SEQ ID No. 22
AEPKSPDKTHTCPPCPKDPK (IgG1 Hinge-Fc)
SEQ ID No. 23
AEPKSPDKTHTCPPCPAPELLGGPSVFLFPPKPKDILMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGKKDPK (IgG1 Hinge Fc modified to remove Fc receptor recognition motifs)
SEQ ID No. 24
AEPKSPDKTHTCPPCPAPP<u>VA</u>*GPSVFLFPPKPKDTLMI<u>A</u>RTPEVTCVVV DVSHEDPEVKFNWYVDGVEVHNAKTKPREEQYNSTYRVVSV<u>U</u>TVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGKKDPK

Modified residues are underlined; * denotes a deletion.

GD2

GD2 is a disialoganglioside expressed on tumors of neuroectodermal origin, including human neuroblastoma and melanoma, with highly restricted expression on normal tissues, principally to the cerebellum and peripheral nerves in humans.

The relatively tumour specific expression of GD2 makes it a suitable target for immunotherapy.

Nucleic Acid Sequence

The second aspect of the invention relates to a nucleic acid sequence which codes for a CAR of the first aspect of the invention.

The nucleic acid sequence may be capable of encoding a CAR having the amino acid sequence shown as any of SEQ ID No. 26-35.

The nucleic acid sequence may be or comprise the following sequence:

```
SEQ ID No. 25 DNA sequence of retroviral cassette comprising of anti-GD2 CAR co-ex-
pressed with
RQR8 suicide gene with a codon-optimized frame and a SAR region to enhance expression
    1 tgaaagaccc cacctgtagg tttggcaagc tagcttaagt aacgccattt tgcaaggcat ggaaaaatac
      >>...........................LTR....................................>

71 ataactgaga atagaaaagt tcagatcaag gtcaggaaca gatggaacag ctgaatatgg gccaaacagg
      >.............................LTR....................................>

141 atatctgtgg taagcagttc ctgccccggc tcagggccaa gaacagatgg aacagctgaa tatgggccaa
      >.............................LTR....................................>

211 acaggatatc tgtggtaagc agttcctgcc ccggctcagg gccaagaaca gatggtcccc agatgcggtc
      >.............................LTR....................................>

281 cagccctcag cagtttctag agaaccatca gatgtttcca gggtgcccca aggacctgaa atgaccctgt
      >.............................LTR....................................>

351 gccttatttg aactaaccaa tcagttcgct tctcgcttct gttcgcgcgc ttatgctccc cgagctcaat
      >.............................LTR....................................>

421 aaaagagccc acaacccctc actcggggcg ccagtcctcc gattgactga gtcgcccggg tacccgtgta
      >.............................LTR....................................>

491 tccaataaac cctcttgcag ttgcatccga cttgtggtct cgctgttcct tgggagggtc tcctctgagt
      >.............................LTR....................................>

561 gattgactac ccgtcagcgg gggtctttca tttgggggct cgtccgggat cgggagaccc ctgcccaggg
      >..............LTR..............>>

631 accaccgacc caccaccggg aggtaagctg gccagcaact tatctgtgtc tgtccgattg tctagtgtct 701 atgactgatt ttatgcgcct gcgtcggtac tagttagcta actagctctg tatctggcgg accgtggtg
                                       Eco52I
                                       ------
  771 gaactgacga gttcggaaca cccggccgca accctgggag acgtcccagg gacttcgggg gccgttttg
          PshAI
          -----------
  841 tggcccgacc tgagtcctaa aatcccgatc gtttaggact ctttggtgca cccccttag aggagggata 911 tgtggttctg gtaggagacg agaacctaaa acagttcccg cctccgtctg aattttgct ttcggtttgg 981 gaccgaagcc gcgccgcgcg tcttgtctgc tgcagcatcg ttctgtgttg tctctgtctg actgtgtttc
                                       SrfI
                                       --------
 1051 tgtatttgtc tgaaaatatg ggcccgggct agcctgttac cactcccctta agtttgacct taggtcactg
```

```
                                      -continued
1121 gaaagatgtc gagcggatcg ctcacaacca gtcggtagat gtcaagaaga gacgttgggt taccttctgc 1191 tctgcagaat ggccaacctt taacgtcgga tggccgcgag acggcacctt taaccgagac ctcatcaccc 1261 aggttaagat caaggtcttt tcacctggcc cgcatggaca cccagaccag gtggggtaca tcgtgacctg 1331 ggaagccttg gcttttgacc ccctccctg ggtcaagccc tttgtacacc ctaagcctcc gcctcctctt 1401 cctccatccg ccccgtctct ccccccttgaa cctcctcgtt cgaccccgcc tcgatcctcc ctttatccag BglII
                                              -------
1471 ccctcactcc ttctctaggc gcccccatat ggccatatga gatcttatat ggggcacccc cgccccttgt 1541 aaacttccct gaccctgaca tgacaagagt tactaacagc ccctctctcc aagctcactt acaggctctc AgeI
                                                                              ------
1611 tacttagtcc agcacgaagt ctggagacct ctggcggcag cctaccaaga caactggac cgaccggtgg 1681 tacctcaccc ttaccgagtc ggcgacacag tgtgggtccg ccgacaccag actaagaacc tagaacctcg AccI
                                                            -------
1751 ctggaaagga ccttacacag tcctgctgac cacccccacc gccctcaaag tagacggcat cgcagcttgg PmlI
              ------
1821 atacacgccg cccacgtgaa ggctgccgac cccggggggtg gaccatcctc tagactgcca acatgggcac
                                                                        >>.orf.>
                                                                        >>RQR8.>

1891 cagcctgctg tgctggatgg ccctgtgcct gctgggcgcc gaccacgccg atgcctgccc ctacagcaac
     >................................orf.................................>
     >................................RQR8.................................>

1961 cccagcctgt gcagcggagg cggcggcagc gagctgccca cccagggcac cttctccaac gtgtccacca
     >................................orf.................................>
     >................................RQR8.................................>

2031 acgtgagccc agccaagccc accaccaccg cctgtcctta ttccaatcct tccctgtgta gcggagggg
     >................................orf.................................>
     >................................RQR8.................................>

2101 aggcagccca gccccagac ctcccacccc agccccacc atcgcagcc agcctctgag cctgagaccc
     >................................orf.................................>
     >................................RQR8.................................>

SgrAI
              ---------
2171 gaggcctgcc gcccagccgc cggcggcgcc gtgcacacca gaggcctgga tttcgcctgc gatatctaca
     >................................orf.................................>
     >................................RQR8.................................>

BclI
                                                                  -------
2241 tctgggcccc actggccggc acctgtggcg tgctgctgct gagcctggtg atcaccctgt actgcaacca
     >................................orf.................................>
     >................................RQR8.................................>

2311 ccgcaaccgc aggcgcgtgt gcaagtgccc caggcccgtg gtgagagccg agggcagagg cagcctgctg
     >................................orf.................................>
     >......................RQR8......................>>
                                                    >>..........FMD-2A..........>

NcoI
              ------
2381 acctgcggcg acgtggagga gaacccaggc cccatggaga ccgacaccct gctgctgtgg gtgctgctgc
     >................................orf.................................>
     >..............FMD-2A...............>>
                                          >>................CAR..................>

2451 tgtgggtgcc aggcagcacc ggccaggtgc agctgcagga gtctggccca ggcctggtga agcccagcca
     >................................orf.................................>
     >................................CAR..................................>

2521 gaccctgagc atcacctgca ccgtgagcgg cttcagcctg ccagctaca acatccactg ggtgcggcag
     >................................orf.................................>
     >................................CAR..................................>
```

-continued

```
2591 cccccaggca agggcctgga gtggctgggc gtgatctggg ctggcggcag caccaactac aacagcgccc
     >...................................orf.......................................>
     >...................................CAR.......................................>

2661 tgatgagccg gctgaccatc agcaaggaca acagcaagaa ccaggtgttc ctgaagatga gcagcctgac
     >...................................orf.......................................>
     >...................................CAR.......................................>

2731 agccgccgac accgccgtgt actactgcgc caagcggagc gacgactaca gctggttcgc ctactggggc
     >...................................orf.......................................>
     >...................................CAR.......................................>

2801 cagggcaccc tggtgaccgt gagctctggc ggaggcggct ctggcggagg cggctctggc ggaggcggca
     >...................................orf.......................................>
     >...................................CAR.......................................>

2871 gcgagaacca gatgacccag agccccagca gcttgagcgc cagcgtgggc gaccgggtga ccatgacctg
     >...................................orf.......................................>
     >...................................CAR.......................................>

2941 cagagccagc agcagcgtga gcagcagcta cctgcactgg taccagcaga gagcggcaa ggccccaaag
     >...................................orf.......................................>
     >...................................CAR.......................................>

3011 gtgtggatct acagcaccag caacctggcc agcggcgtgc ccagccggtt cagcggcagc ggcagcggca
     >...................................orf.......................................>
     >...................................CAR.......................................>

3081 ccgactacac cctgaccatc agcagcctgc agcccgagga cttcgccacc tactactgcc agcagtacag
     >...................................orf.......................................>
     >...................................CAR.......................................>

BamHI
                                                                               ------
3151 cggctacccc atcaccttcg gccagggcac caaggtggag atcaagcggt cggatcccgc cgagcccaaa
     >...................................orf.......................................>
     >...................................CAR.......................................>

FseI
                                                                      ---------
3221 tctcctgaca aaactcacac atgcccaccg tgcccagcac ctcccgtggc cggcccgtca gtcttcctct
     >...................................orf.......................................>
     >...................................CAR.......................................>

3291 tccccccaaa acccaaggac accctcatga tcgcccggac ccctgaggtc acatgcgtgg tggtggacgt
     >...................................orf.......................................>
     >...................................CAR.......................................>

3361 gagccacgaa gaccctgagg tcaagttcaa ctggtacgtg gacggcgtgg aggtgcataa tgccaagaca
     >...................................orf.......................................>
     >...................................CAR.......................................>

SacII
        ------
3431 aagccgcggg aggagcagta caacagcacg taccgtgtgg tcagcgtcct caccgtcctg caccaggact
     >...................................orf.......................................>
     >...................................CAR.......................................>

3501 ggctgaatgg caaggagtac aagtgcaagg tctccaacaa agccctccca gcccccatcg agaaaaccat
     >...................................orf.......................................>
     >...................................CAR.......................................>

3571 ctccaaagcc aaagggcagc cccgagaacc acaggtgtac accctgcccc catcccggga tgagctgacc
     >...................................orf.......................................>
     >...................................CAR.......................................>

3641 aagaaccagg tcagcctgac ctgcctggtc aaaggcttct atcccagcga catcgccgtg gagtgggaga
     >...................................orf.......................................>
     >...................................CAR.......................................>

3711 gcaatgggca accggagaac aactacaaga ccacgcctcc cgtgctggac tccgacggct ccttcttcct
     >...................................orf.......................................>
     >...................................CAR.......................................>
```

-continued

```
                                                                    Ppu10I
                                                                    ------
                                                                     NsiI
                                                                    ------
                                                                    BfrBI
                                                                    ------
3761 ctacagcaag ctcaccgtgg acaagagcag gtggcagcag gggaacgtct tctcatgctc cgtgatgcat
     >..................................orf.................................>
     >..................................CAR.................................>

Van91I
                                                                    ----------
3851 gaggccctgc acaatcacta tacccagaaa tctctgagtc tgagcccagg caagaaggac cccaagttct
     >..................................orf.................................>
     >..................................CAR.................................>

3921 gggtcctggt ggtggtggga ggcgtgctgg cctgttactc tctcctggtg accgtggcct tcatcatctt
     >..................................orf.................................>
     >..................................CAR.................................>

3991 ctgggtgcgc tccaagagga gcaggctcct gcacagtgac tacatgaaca tgactccccg ccgccccggg
     >..................................orf.................................>
     >..................................CAR.................................>

4061 cccacccgca agcattacca gccctatgcc ccaccacgcg acttcgcagc ctatcgctcc cgggtgaagt
     >..................................orf.................................>
     >..................................CAR.................................>

4131 tctctcgctc tgccgatgcc ccagcctatc agcagggcca gaatcagctg tacaatgaac tgaacctggg
     >..................................orf.................................>
     >..................................CAR.................................>

4201 caggcgggag gagtacgacg tgctggataa gcggagaggc agagaccccg agatgggcgg caaaccacgg
     >..................................orf.................................>
     >..................................CAR.................................>

4271 cgcaaaaatc cccaggaggg actctataac gagctgcaga aggacaaaat ggccgaggcc tattccgaga
     >..................................orf.................................>
     > GAR >

4341 tcggcatgaa gggagagaga agacgcggaa agggccacga cggcctgtat cagggattgt ccaccgctac
     >..................................orf.................................>
     >..................................CAR.................................>

MluI ClaI
                                                          ------------
4411 aaaagataca tatgatgccc tgcacatgca ggccctgcca cccagatgac gcgtatcgat actgttctca
     >......................orf.....................>>
     >......................CAR.....................>>
                                                                >>...SAR..>

4481 tcacatcata tcaaggttat ataccatcaa tattgccaca gatgttactt agccttttaa tatttctcta
     >..................................SAR.................................>

4551 atttagtgta tatgcaatga tagttctctg atttctgaga ttgagtttct catgtgtaat gattatttag
     >..................................SAR.................................>

4621 agtttctctt tcatctgttc aaattttgt ctagttttat tttttactga tttgtaagac ttcttttat
     >..................................SAR.................................>

4691 aatctgcata ttacaattct ctttactggg gtgttgcaaa tattttctgt cattctatgg cctgactttt
     >..................................SAR.................................>

4761 cttaatggtt ttttaatttt aaaaataagt cttaatattc atgcaatcta attaacaatc ttttctttgt
     >..................................SAR.................................>

SphI
                                                                    ------
4831 ggttaggact ttgagtcata agaaattttt ctctacactg aagtcatgat ggcatgcttc tatattattt
     >..................................SAR.................................>

4901 tctaaaagat ttaaagtttt gccttctcca tttagactta taattcactg gaattttttt gtgtgtatgg
     >..................................SAR.................................>

4971 tatgacatat gggttcccct ttattttta catataaata tatttccctg ttttctaaa aagaaaaag
     >..................................SAR.................................>

5041 atcatcattt tcccattgta aaatgccata ttttttcat aggtcactta catatatcaa tgggtctgtt
     >..................................SAR.................................>
```

```
-continued
5111 tctgagctct actctattt atcagcctca ctgtctatcc ccacacatct catgctttgc tctaaatctt
     >...................................SAR....................................>

5181 gatatttagt ggaacattct ttcccatttt gttctacaag aatatttttg ttattgtctt tgggctttct
     >...................................SAR....................................>

5251 atatacattt tgaaatgagg ttgacaagtt cggattagtc caatttgtta aagacaggat atcagtggtc
     >...............SAR...............>>

5321 caggctctag ttttgactca acaatatcac cagctgaagc ctatagagta cgagccatag ataaaataaa 5391 agattttatt tagtctccag aaaaaggggg gaatgaaaga ccccacctgt aggtttggca agctagctta
                                             >>.................LTR.................>

5461 agtaacgcca ttttgcaagg catggaaaaa tacataactg agaatagaga agttcagatc aaggtcagga
     >....................................LTR....................................>

5531 acagatggaa cagctgaata tgggccaaac aggatatctg tggtaagcag ttcctgcccc ggctcagggc
     >....................................LTR....................................>

5601 caagaacaga tggaacagct gaatatgggc caaacaggat atctgtggta agcagttcct gccccggctc
     >....................................LTR....................................>

5671 agggccaaga acagatggtc cccagatgcg gtccagccct cagcagtttc tagagaacca tcagatgttt
     >....................................LTR....................................>

5741 ccagggtgcc ccaaggacct gaaatgaccc tgtgccttat ttgaactaac caatcagttc gcttctcgct
     >....................................LTR....................................>

5611 tctgttcgcg cgcttctgct ccccgagctc aataaaagag cccacaaccc ctcactcggg gcgccagtcc
     >....................................LTR....................................>

5881 tccgattgac tgagtcgccc gggtacccgt gtatccaata aaccctcttg cagttgcatc cgacttgtgg
     >....................................LTR....................................>

5951 tctcgctgtt ccttgggagg gtctcctctg agtgattgac tacccgtcag cgggggtctt tcac
     >...................LTR................>>
```

The nucleic acid sequence may encode the same amino acid sequence as that encoded by SEQ ID No. 25, but may have a different nucleic acid sequence, due to the degeneracy of the genetic code. The nucleic acid sequence may have at least 80, 85, 90, 95, 98 or 99% identity to the sequence shown as SEQ ID No. 25, provided that it encodes a CAR as defined in the first aspect of the invention.

Suicide Genes

Since T-cells engraft and are autonomous, a means of selectively deleting CAR T-cells in recipients of anti-GD2 CAR T-cells is desirable. Suicide genes are genetically encodable mechanisms which result in selective destruction of infused T-cells in the face of unacceptable toxicity. The earliest clinical experience with suicide genes is with the Herpes Virus Thymidine Kinase (HSV-TK) which renders T-cells susceptible to Ganciclovir. HSV-TK is a highly effective suicide gene. However, pre-formed immune responses may restrict its use to clinical settings of considerable immunosuppression such as haploidentical stem cell transplantation. Inducible Caspase 9 (iCasp9) is a suicide gene constructed by replacing the activating domain of Caspase 9 with a modified FKBP12. iCasp9 is activated by an otherwise inert small molecular chemical inducer of dimerization (CID). iCasp9 has been recently tested in the setting of haploidentical HSCT and can abort GvHD. The biggest limitation of iCasp9 is dependence on availability of clinical grade proprietary CID. Both iCasp9 and HSV-TK are intracellular proteins, so when used as the sole transgene, they have been co-expressed with a marker gene to allow selection of transduced cells.

An iCasp9 may comprise the sequence shown as SEQ ID No. 36 or a variant thereof having at least 80, 90, 95 or 98% sequence identity.

SEQ ID No. 36
MLEGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHATL

VFDVELLKLESGGGSGVDGFGDVGALESLRGNADLAYILSMEPCGHCLII

NNVNFCRESGLRTRTGSNIDCEKLRRRFSSLHFMVEVKGDLTAKKMVLAL

LELAQQDHGALDCCVVVILSHGCQASHLQFPGAVYGTDGCPVSVEKIVNI

FNGTSCPSLGGKPKLFFIQACGGEQKDHGFEVASTSPEDESPGSNPEPDA

TPFQEGLRTFDQLDAISSLPTPSDIFVSYSTFPGFVSWRDPKSGSWYVET

LDDIFEQWAHSEDLQSLLLRVANAVSVKGIYKQMPGCFNFLRKKLFFKTS

AS

The present inventors have recently described a novel marker/suicide gene known as RQR8 which can be detected with the antibody QBEnd10 and expressing cells lysed with the therapeutic antibody Rituximab.

An RQR8 may comprise the sequence shown as SEQ ID No. 37 or a variant thereof having at least 80, 90, 95 or 98% sequence identity.

SEQ ID No. 37
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVV

The suicide gene may be expressed as a single polypeptide with the CAR, for example by using a self-cleaving peptide between the two sequences.

Vector

The present invention also provides a vector which comprises a nucleic acid sequence according to the present invention. Such a vector may be used to introduce the nucleic acid sequence into a host cell so that it expresses and produces a molecule according to the first aspect of the invention.

The vector may, for example, be a plasmid or a viral vector, such as a retroviral vector or a lentiviral vector.

The vector may be capable of transfecting or transducing a T cell.

The vector may also comprise a nucleic acid sequence encoding a suicide gene, such as iCasp9 or RQR8.

Host Cell

The invention also provides a host cell which comprises a nucleic acid according to the invention. The host cell may be capable of expressing a CAR according to the first aspect of the invention.

The host cell may be a cytolytic immune cell such as a human T cell or natural killer (NK) cell.

A T-cell capable of expressing a CAR according to the invention may be made by transducing or transfecting a T cell with CAR-encoding nucleic acid.

The CAR T-cell may be generated ex vivo. The T cell may be from a peripheral blood mononuclear cell (PBMC) sample from the patient or a donor. T cells may be activated and/or expanded prior to being transduced with CAR-encoding nucleic acid, for example by treatment with an anti-CD3 monoclonal antibody.

Pharmaceutical Composition

The present invention also relates to a pharmaceutical composition containing a vector or a CAR-expressing T cell of the invention together with a pharmaceutically acceptable carrier, diluent or excipient, and optionally one or more further pharmaceutically active polypeptides and/or compounds. Such a formulation may, for example, be in a form suitable for intravenous infusion).

Method of Treatment

T cells expressing a CAR molecule of the present invention are capable of killing cancer cells, such as neurobastoma cells. CAR-expressing T cells may either be created ex vivo either from a patient's own peripheral blood ($1^{st}$ party), or in the setting of a haematopoietic stem cell transplant from donor peripheral blood ($2^{nd}$ party), or peripheral blood from an unconnected donor ($3^{rd}$ party). Alternatively, CAR T-cells may be derived from ex-vivo differentiation of inducible progenitor cells or embryonic progenitor cells to T-cells. In these instances, CAR T-cells are generated by introducing DNA or RNA coding for the CAR by one of many means including transduction with a viral vector, transfection with DNA or RNA.

T cells expressing a CAR molecule of the present invention may be used for the treatment of a cancerous disease, in particular a cancerous disease associated with GD2 expression.

The cancer may be an ectodermal tumour.

Examples of cancers which correlate with elevated GD2 expression levels are: neuroblastoma, melanoma, medulloblastoma, soft-tissue sarcomas, osteosarcoma and small-cell lung cancers such as NSCLC.

A method for the treatment of disease relates to the therapeutic use of a vector or T cell of the invention. In this respect, the vector or T cell may be administered to a subject having an existing disease or condition in order to lessen, reduce or improve at least one symptom associated with the disease and/or to slow down, reduce or block the progression of the disease. The method of the invention may cause or promote T-cell mediated killing of GD2-expressing cells, such as cancer cells.

GD2 Expressing Cell

The invention also provides a method for making a GD2-expressing cell which comprises the step of introducing a nucleic acid encoding GM3 synthase and a nucleic acid encoding GD2 synthase into a cell.

The nucleic acid may be introduced by, for example, transfection or transduction, using a vector such as a plasmid or viral vector.

The invention also relates to a GD2-expressing cell which comprises a heterologous nucleic acid encoding GM3 synthase and a heterologous nucleic acid encoding GD2 synthase.

The nucleic acid may be "heterologous" in the sense that it is not usually present in the cell. It is an artificially introduced recombinant nucleic acid sequence.

The cell may be from a cell line.

The cell may be used for stimulating GD2CAR T-cells in culture, such as the T cells of the present invention.

The invention will now be further described by way of Examples, which are meant to serve to assist one of ordinary skill in the art in carrying out the invention and are not intended in any way to limit the scope of the invention.

EXAMPLES

Example 1—Using the Humanized Antibody huK666 as a Binder

Figure 3:
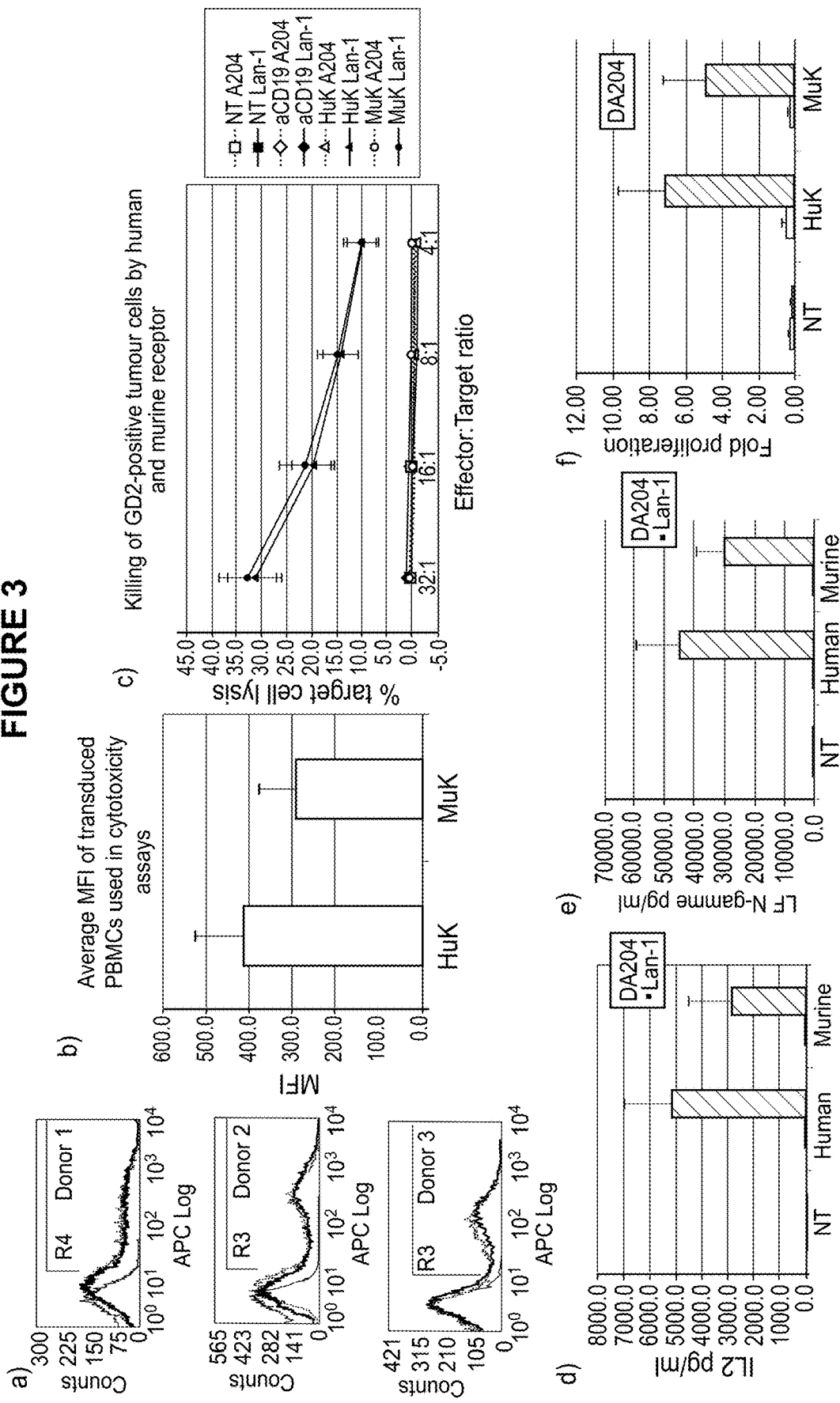
FIG. 3—Comparison of muKM666 and huKM666 based CARs. (a) Expression on peripheral blood T-cells from 3 normal donors; (b) mean-fluorescent intensity of these facs plots shown as a histogram; (c) Chromium release assay using non-transduced, muKM666 and huKM666 transduced T-cells as effectors against A204 (GD2 negative), and LAN-1 (GD2 positive) targets; (d) IL-2 production from the same challenge; (e) Interferon-gamma production from the same challenge; and (f) Fold-proliferation from the same challenge.

CARs were constructed with scFvs using sequences from either the mouse antibody KM666 or its humanized version huK666 as described by Nakamura et al (2001—as above) (variants (a) and (b) in FIG. 2 above). These receptors were compared for expression/stability and found to be equal for both receptors. Next, killing, cytokine release and proliferation of T-cells transduced with these receptors were tested when challenged by target cells either not expressing or expressing GD2. It was concluded that killing of both receptors was similar, but the humanized scFv based receptor resulted in superior 11_2 production and proliferation (FIG. 3).

Example 2—Testing the Effect of Different Spacer Formats Effects on Expression and Function Anti-GD2 CARs with Fc spacer, Hinge, Hinge-CD8 stalk and Cd8 stalk were generated (FIGS. 2 (b), (d), (e) and (f) respectively). These CARs were co-expressed with the marker gene, truncated CD34, in an obligate 1:1 fashion with the 2A foot-and-mouth self-cleaving peptide to allow accurate comparison (FIG. 4a). Further, the huK666 scFv was tagged with an aminoterminal HA tag to allow comparison of transgene versus CAR expression.

Flow cytometric analysis of normal donor T-cells transduced with these constructs demonstrated brighter CAR expression in the following order: Fc>Hinge-stalk=stalk>Hinge (FIG. 4b).

Killing of GD2 positive targets relative to GD2 negative targets was compared using chromium release assays. This showed killing effectiveness in the following order: Fc>Hinge-stalk=stalk>Hinge (FIG. 4c).

Interferon-gamma release and IL-2 release was compared when CAR T-cells were challenged with either GD2 positive or negative targets. Inteferon-gamma release was similar in CARs with Fc, hinge-stalk and stalk but less in the hinge variant. IL2 release was detected in the following order: Fc, stalk, hinge-stalk, hinge (FIGS. 4d and e).

Finally, proliferation of CAR T-cells was compared when CAR T-cells were challenged with either GD2 positive or negative targets. Proliferation was detected in the following order: Stalk, hinge-stalk, Fc, hinge (FIGS. 4d and e)

Example 3—FcR Mutations Abrogate Non-Specific Activity

Figure 5:
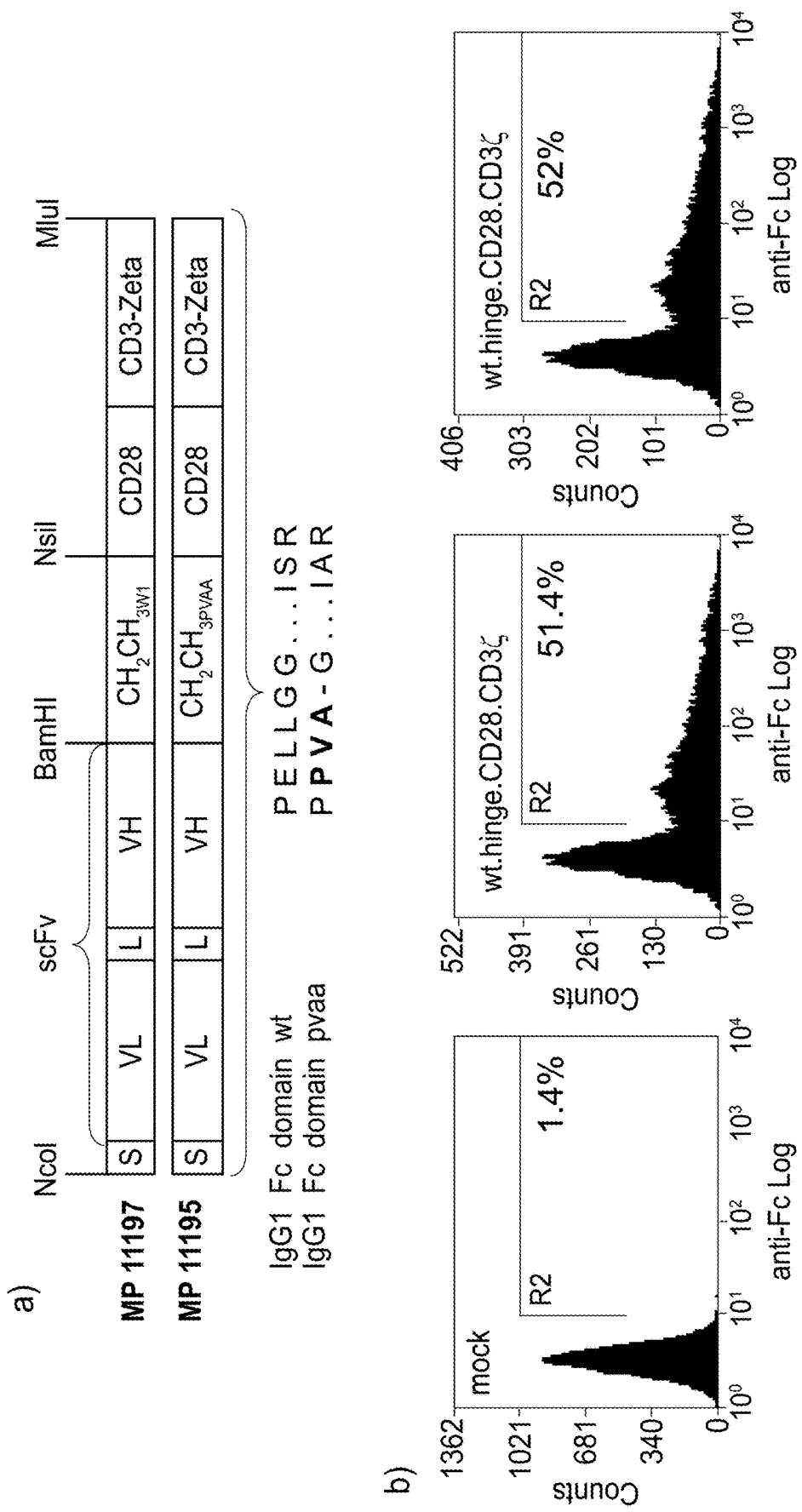
FIG. 5—Introduction of FcR binding disrupting mutations into the Fc spacer (a) mutations introduced; (b) Expression of CAR as determined by anti-Fc staining: non-transduced, wt and mutated; (c) Killing of GD2 negative and GD2 positive targets with either non-transduced, wt Fc and mutated Fc anti-GD2 CAR T-cells; (d) Activation of non-transduced, wt Fc and mutated Fc anti-GD2 T-cells with the FcR expressing cell line THP-1; IL-1Beta release by THP-1 cell line in response to non-transduced, wt Fc and mutated Fc CAR T-cells.
Figure 5:
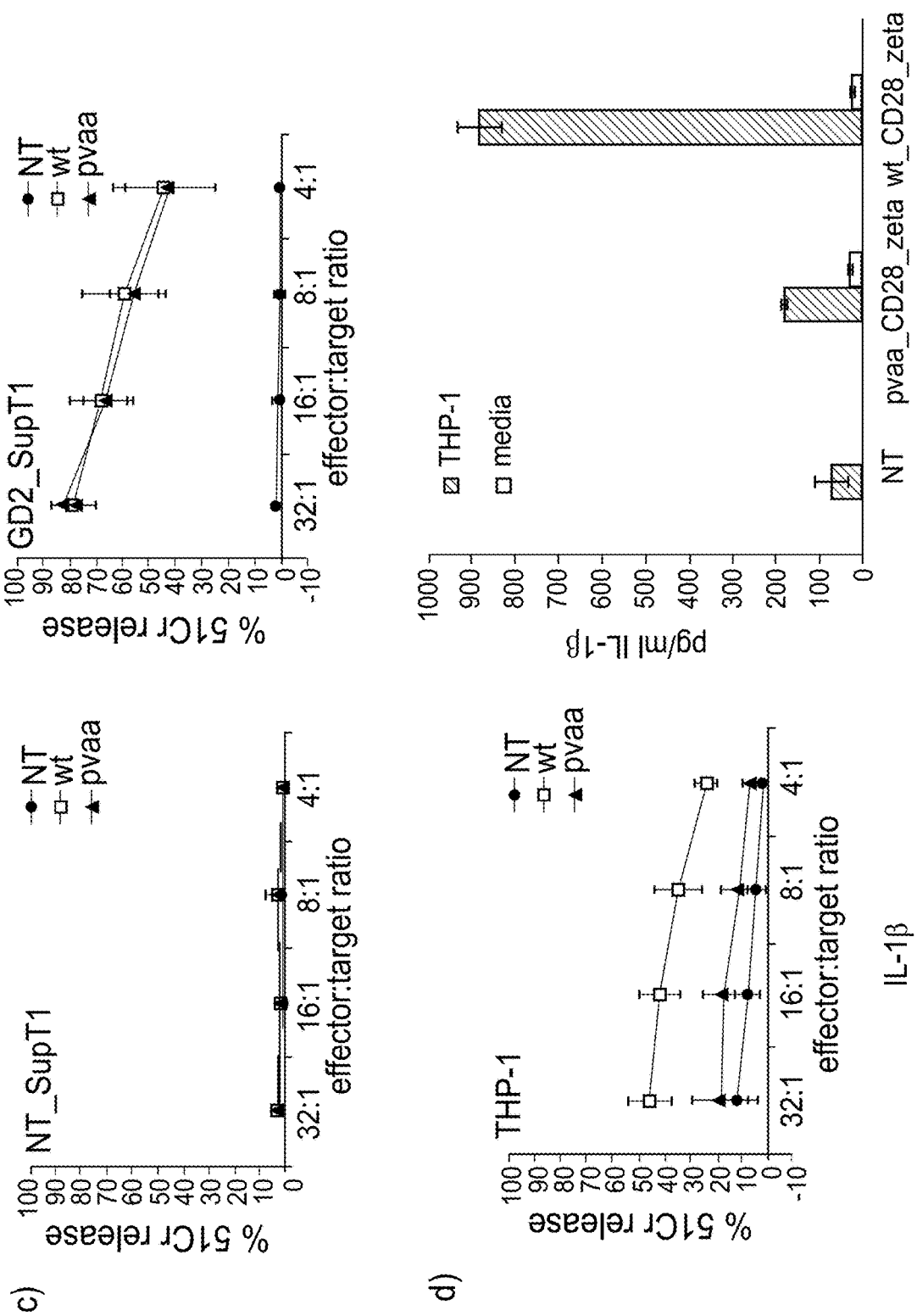

The overall data from the above Examples suggested that the Fc spacer performs best overall. However the Fc domain in vivo may lead to non-specific activation from cells which express Fc receptors. To abrogate this effect, mutations were introduced into the Fc region as shown in FIG. 5(a). These mutations had no deleterious effects on CAR expression, as shown in FIG. 5(b).

In addition, it was shown that these mutations had no effect on CAR killing function (FIG. 5(c)). Finally, it was shown that these mutations had the desired effect in terms of non-specific killing of FcR expressing targets (a monocytoid line called THP1), and IL-1Beta release by these monocytes (FIG. 5e).

Example 4—Optimization of the Expression Cassette

With a view to optimising expression of the receptor, the following were tested: (a) inclusion of a scaffold attachment region (SAR) into the cassette; (b) inclusion of chicken beta hemoglobin chromatin insulator (CHS4) into the 3'LTR and (c) codon optimization of the open reading frame (FIG. 6a). It was shown that inclusion of a SAR improved the nature of expression as did codon-optimization while the CHS4 had little effect (FIG. 6b). Combining SAR and codon-optimization improved expression additively (FIG. 6c)

Example 5—Comparison of Different Endodomains

Figure 7:
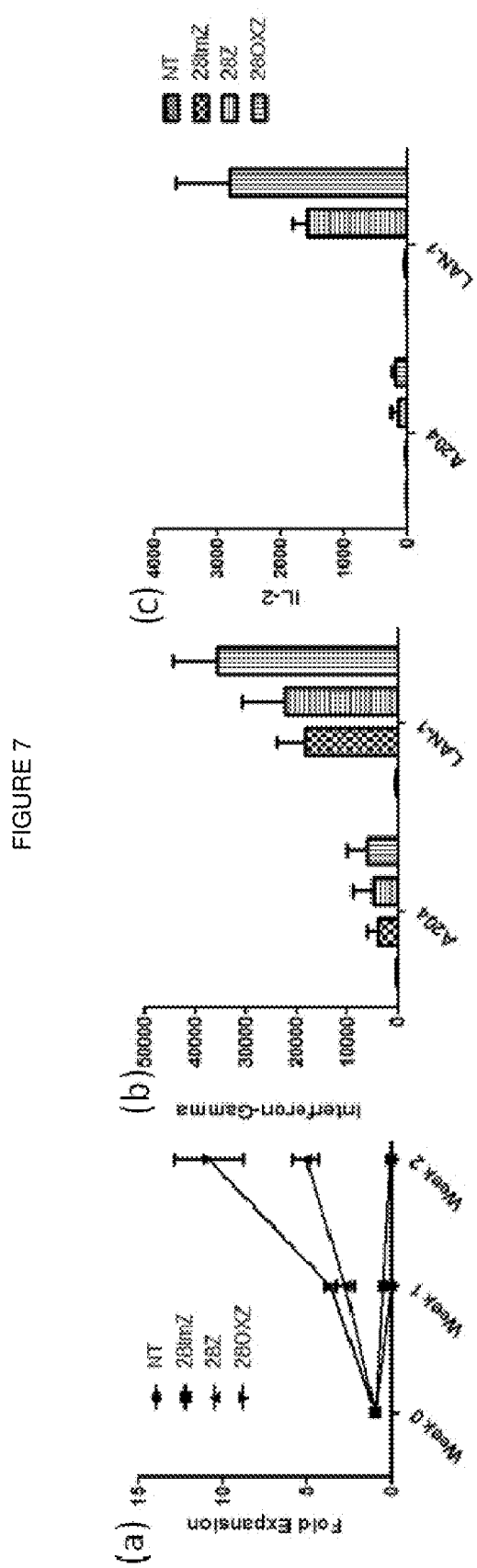
FIG. 7—Comparison of different endodomains

Constructs with three different endodomains were generated: CD28 trans-membrane domain with CD3-zeta endodomain (CD28tmZ); CD28 transmembrane domain with CD28 endodomain and CD3-zeta endodomain (CD28Z), and CD28 transmembrane domain, CD28 endodomain, OX30 endodomain and CD3-zeta endodomain (CD28OXZ) with a CAR in the Fc spacer format. Proliferation, IFNγ release and IL-2 release were noted to increase in order of CD28tmZ<CD28Z<CD28OXZ (FIG. 7).

Example 6—Co-Expression with iCasp9 Suicide Gene

The iCasp9 suicide gene was co-expressed with the anti-GD2 CAR (FIG. 8a—the CAR was in the format of Fc-spacer, CD28OXZ chosen arbitrarily to demonstrate function). The CAR could be well-expressed despite co-expression with iCasp9 (FIG. 8b). Activation of iCasp9 with the small molecular dimerizer led to deletion of CAR positive T-cells (FIG. 8b). iCasp9-GD2CAR T-cells exposed to this dimerizer lost their GD2 specificity when exposed to the dimerizer (FIG. 8c).

Example 7—Co-Expression with RQR8 Suicide Gene

The anti-GD2 CAR was co-expressed with the RQR8 sort-suicide gene. (FIG. 9a—the CAR was in the format of Fc-spacer, CD28Z chosen arbitrarily to demonstrate function). It was possible to co-express receptor and CAR (FIG. 9b). Activation of the suicide gene function of RQR8 with Rituximab and complement resulted in deletion of transduced T-cells and loss of GD2 recognition (FIGS. 9c and d).

Example 8—Expression of GD2 Synthase and GM3 Synthase Results in GD2 Expression in any Cell Line In order to stimulate GD2CAR T-cells in culture, to have ideal GD2- or GD2+ targets, and to be able to generate syngeneic cells for small animal models, it is desirable to be able to transgenically express GD2 on a cell line. GD2 is not a protein and needs to be synthesized by a complex set of enzymes. Here it is shown that transgenic expression of just two enzymes: GM3synthase and GD2synthase results in bright GD2 expression in all cell lines transduced thus far (FIG. 10).

Example 9—In Vivo Function of Anti-GD2 CAR

CT26 cell line was engineered to express GD2 as described above (designated CT26 clone #7 or CT25#7 for short). Either $2 \times 10^5$ of wild type (wt) or GD2 positive CD26 cells were inoculated into the flanks of C57BL/6 mice (syngeneic with CT26). 10 days after tumour challenge, mock-transduced and anti-GD2 CAR transduced syngeneic splenocytes were prepared. Mice were divided into the following 4 cohorts: mice with GD2 expressing CT26 tumours receiving anti-GD2 CAR spleoncytes; GD2 expressing CT26 tumours receiving mock-transduced splenocytes; GD2 negative (wt) CT26 tumours with anti-GD2 CAR splenocytes; and GD2 expressing CT26 tumours receiving no splenocytes. Tumour was measured using a digital caliper in 3 dimension and volume estimated therewith. FIG. 11 shows the growth curves of the tumours. Only GD2 positive tumours in mice receiving anti-GD2 CAR T-cells had little or no growth.

Example 10—Comparing the Function of CARs Comprising huK666 and 14g2a-Based Antigen Binding Domains The antigen binding domain of a CAR can affect its function. In this study, the function of the CAR of the invention with an antigen-binding domain based on huK666 with a CAR was compared with an equivalent CAR having an antigen-binding domain based on 14g2a.

The antibody 14g2a can be seen as the gold standard antibody against GD2 since it is used as a therapeutic mAb and it is the only scFv tested in a CAR study.

Second generation CARs were constructed and expressed based on huK666 or 14g2a. Their structure is shown in FIG. 14a.

Retroviruses were produced by transient transfection of 293T cells with plasmids encoding the GD2 CARs, gag/pol and the envelope protein RD114. After 3 days the supernatants were harvested and used to transduce PHA/IL2-activated PBMCs with equal titres of retrovirus on retronectin-coated plates. The CARs differed solely in their antigen binding domain. In both cases the binding domains were linked to the membrane with an IgG Fc segment and contained intracellular activatory motifs from CD28 and CD3-zeta. Six days post-transduction CAR-expression was confirmed by flow cytometry and PBMCs were cultured in a 1:1 ratio with GD2-positive Lan1 cells (a GD2 positive cell line) or GD2-negative A204 cells (a GD2 negative rhabdomyosarcoma cell line). After one day supernatants from these co-cultures were assayed for interferon-γ levels by ELISA and T cell proliferation was assessed by flow cytometry after 6 days.

The results are shown in FIGS. 14 and 15. At 24 hours, Interferon-gamma was measured from supernatant. huK666 CAR T-cells were shown to produce more IFN-γ (FIG. 14b). After one week T-cells were counted, and the huK666 CAR was show to have more proliferation (FIG. 14c).

After one week of co-culture with the Neuroblastoma cell line LAN1, cells were harvested and analyzed by flow-cytometry. CD45 expression allowed discrimination from lymphoid cells and non-lymphoid cells with CD45– cells being LAN-1 cells. Further staining with CD3/QBEND/10 allowed counting of CAR T-cells. It was found that huK666 CAR T-cells proliferate better and kill more completely than 14g2a equivalents (FIG. 15).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for treating cancer which comprises the step of administering a T cell to a subject,
   wherein the T cell expresses a chimeric antigen receptor (CAR) comprising
   a) a disialoganglioside (GD2)-binding domain and spacer, shown as amino acids 21 to 311 of SEQ ID NO: 29,
   b) a hydrophobic alpha helical transmembrane domain, and
   c) a CD28-CD3Zeta endodomain shown as SEQ ID NO: 17; and
   wherein the cancer is a melanoma, medulloblastoma, soft-tissue sarcoma, osteosarcoma or small-cell lung cancer.

2. The method of claim 1 wherein the cancer is a small-cell lung cancer.

* * * * *